United States Patent [19]

Zasloff et al.

[11] Patent Number: 5,432,270

[45] Date of Patent: Jul. 11, 1995

[54] DNA ENCODING TRACHEAL ANTIMICROBIAL PEPTIDES

[76] Inventors: Michael A. Zasloff, 274 Linden La., Merion, Pa. 19066; Charles L. Bevins, 528 Lombardy St., Drexel Hill, Pa. 19026; Gill Diamond, 7351 Ruskin Rd., Philadelphia, Pa. 19151

[21] Appl. No.: 60,822

[22] Filed: May 11, 1993

Related U.S. Application Data

[63] Continuation-in-part of Ser. No. 991,200, Dec. 15, 1992, abandoned, which is a continuation of Ser. No. 603,451, Oct. 25, 1990, Pat. No. 5,202,420.

[51] Int. Cl.$^6$ ............................................. C12N 15/12
[52] U.S. Cl. .................................. 536/23.5; 536/24.31
[58] Field of Search ........................... 536/23.5, 24.31; 435/320.1, 240.2, 252.3, 69.1

[56] References Cited

U.S. PATENT DOCUMENTS 4,399,216  8/1983  Axel ........................................ 435/6
4,677,063  6/1987  Mark et al. ........................ 435/172.3
5,210,027  5/1993  Wilde et al. ......................... 435/69.1

FOREIGN PATENT DOCUMENTS 60-78996  5/1985  Japan .

OTHER PUBLICATIONS

Ganz et al. "The Structure of the Rabbit Macrophage Defensin Genes . . . " *J. Immunol* 143(4):1358–1365 (Aug. 1989).
Daher et al., "Isolation and Characterization of Human Defensin cDNA Clones", *PNAS* 85:7327–7331 (Oct. 1988).
Noda et al., "Cloning and Sequence Analysis of Calf cDNA . . . " *Nature* 305:818–823 (Oct. 1983).
Sasaki et al., "Cloning and Expression of a Complementary DNA . . ." *Nature* 351:230–233 (May 1991).
Aldridge et al., "A Strategy to Reveal High-Frequency RFLPs Along the Human X Chromosome", *Am. J. Hum. Genet.* 36:546–564 (1984).
Ausubel et al., *Current Protocols in Molecular Biology* vol. 1, "DNA–Dependent RNA Polymerases", 3.8.1–3.8.4 (Mass. General Hospital) (1987).
Bevins and Zasloff, "Peptides from Frog Skin," *Ann. Rev. Biochem.*, 59:399–414 (1990).
Boman and Hultark, "Cell–Free Immunity in Insects", *Ann. Rev. Microbiol.* 41:103–126 (1987).
Broach et al., "Transformation in Yeast: Development of a Hybrid Cloning Vector and Isolation of the CAN1 Gene", *Gene* 8: 121–133 (1979).
Broach, "Construction of High Copy Yeast Vectors Using 2-μm Circle Sequences", *Meth Enz.* 101:307–325 (1983).
Chirgwin et al., "Isolation of Biologically Active Ribonucleic Acid from Sources Enriched in Ribonuclease," *Biochem.* 18:5294–5299 (1979).
Clarke et al., "Selection Procedure for Isolation of Centromere DNAs from *Sacchromyces cerevisiae*", *Meth Enz* 101:300–307 (1983).
Clewell, "Nature of Col E$_1$ Plasmid Replication in *Escherichia coli* in the Presence of Chrloramphenicol", *J. Bacteriol* 110:657–676 (1972).
Clewell et al., "Supercoiled Circular DNA–protein Complex in *Escherichia Coli*: Purification and Induced Conversion to an Open Circular DNA Form", *Proc Natl. Acad. Sci.* (USA) 62:1159–1166 (1969).
Cohen, "Nonchromosomal Antibiotic Resistance in Bacteria: Genetic Transformation of *Escherichia coli* by R-Factor DNA", *Proc. Natl. Acad. Sci.* (USA) 69:2110–2114 (1972).
Devereux et al., "A Comprehensive Set of Sequence Analysis Programs for the VAX," *Nucl. Acids Res.* 12:387–395 (1984).

(List continued on next page.)

*Primary Examiner*—Stephen G. Walsh
*Attorney, Agent, or Firm*—Woodcock, Washburn, Kurtz, Mackiewicz & Norris

[57] ABSTRACT

The present invention provides a new class of polypeptides with antimicrobial activity, termed "tracheal antimicrobial peptides," DNA and cDNA sequences encoding for the peptides and methods for the production and use thereof.

3 Claims, 15 Drawing Sheets

OTHER PUBLICATIONS

Diamond et al., "Tracheal Antimicrobial Peptide, a Cysteine-Rich Peptide from Mammalian Tracheal Mucosa: Peptide Isolation and Clining of a cDNA", *Proc. Natl. Acad. Sci.* (USA) 88:3952–3956 (1991).

Duncan, "Novel Alu-Type Repeat in Artiodactyls", *Nuc. Acids. Res.* 15:1340 (1987).

Fiers et al., "Complete Nucleotide Sequence of SV40 DNA", *Nature* 273:113–120 (1978).

Fujiwara et al., "A Potent Antimicrobial Protein in Royal Jelly," *J. Biol. Chem.* 265:11333–11337 (1990).

Gabay, "Microbicidal Mechanisms of Phagocytes," *Curr. Opin. Immunol.,* 1:36–40 (1988).

Gabay et al., "Antibiotic Proteins of Human Polymorphonuclear Leukocytes," *Proc. Natl. Acad. Sci. USA* 86:5610–5614 (1989).

Ganz, "Extracellular Release of Antimicrobial Defensins by Human Polymorphonuclear Leukocytes," *Infect Immun* 55:568–571 (1987).

Ganz et al., "Microbicidal/Cytotoxic Proteins of Neutrophils are Deficient in Two Disorders: Chediak-Higashi Syndrome and Specific Granule Deficiency," *J. Clin. Invest.* 82:552–556 (1988).

Ganz et al., "Defensins," *Eur. J. Haematol* 44:1–8 (1990).

Ganz et al., "Defensins. Natural Peptide Antibodies of Human Neutrophils," *J. Clin. Invest.* 76::1427–1435 (1985).

Graham and van der Eb, "A New Technique for the Assay of Infectivity of Human Adenovirus 5 DNA", *Virology* 52:456–467 (1973).

Hess et al., "Cooperation of Glycolytic Enzymes", *J. Adv. Enzyme Reg.* 7:149–167 (1968).

Hitzeman, et al., "Isolation and Characterization of the Yeast 3-Phosphoglycerokinase Gene (PGK) by an immunological Screening Technique", *J. Biol. Chem.* 255:2073 (1980).

Holland and Holland, "Isolation and Identification of Yeast Messenger Ribonucleic Acids Coding for Enolase, Glyceraldehyde-3-Phosphate Dehydrogenase, and Phosphoglycerate Kinase", *Biochemistry* 17:4900–4907 (1978).

Holland et al., "The Primary Structures of Two Yeast Enolase Genes", *J. Biol. Chem.* 256:1385–1395 (1981).

Hsiao and Carbon, "High-Frequency Transformation of Yeast by Plasmids Containing the Cloned Yeast ARG4 Gene", *Proc. Natl. Acad. Sci.* (USA) 76:3829–3833 (1979).

Jones and Bevins, "Paneth Cells of the Human Small Intestine Express an Antimicrobial Peptide Gene", *J. Biol. Chem.* 267:23216–23225 (1992).

Kagan et al., "Antimicrobiol Defensin Peptides Form Voltage-Dependent Ion-Permeable Channels in Planar Lipid Bilayer Membranes," *Proc. Natl. Acad. Sci. USA* 87:210–214 (1990).

Kylsten et al., "The Cecropin Locus in Drosophila; a Compact Gene Cluster Involved in the Response to Infection", *EMBO Journal* 9:217–224 (1990).

Lathe, R. "Synthetic Oligonucleotide Probes Deduced from Amino Acid Sequence Data. Theoretical and Practical Considerations," *J. Mol. Biol.* 183:1–12 (1985).

Lambert et al., "Insect Immunity:Isolation From Immune Blood of the Dipteran Phormia Terranovae of Two Insect Antibacterial Peptides with Sequence Homology to Rabbit Lung Macrophage Bactericidal Peptides" *Proc. Natl. Acad. Sci. USA 86(1):262–266 (1989).*

Lambert et al., "Insect Immunity:Isolation From Immune Blood of the Dipteran Phormia Terranovae of Two Insect Antibacterial Peptides with Sequence Homology to Rabbit Lung Macrophage Bactericidal Peptides" [published erratum appears in *Proc. Natl. Acad. Sci. USA* May;86 (9):3321(1989)].

Lehrer, R. I., T. Ganz et al., "Oxygen-independent Bactericidal Systems. Mechanisms and Disorders," *Hematol. Oncol. Clin. Nort. Am.* 2:159–169 (1988).

Lehrer et al., "Interaction of Human Defensins with Escherichia Coli. Mechanism of Bactericidal Activity," *J. Clin. Invest.* 84::553–561 (1989).

Lenardo and Baltmore, "NF-κB: A Pleiotropic Mediator of Inducible and Tissue-Specific Gene Control", *Cell* 58 :227–229 (1990).

Lindholdm et al. "Insect Immunity: cDNA Clones Coding for the Precursor Forms of Cecropins A and D, Antibacterial Proteins from Hyalophora Cecropia", *F.E.B.S. Lett.* 226:8–12 (1987).

Lipmann, D. J. and W. R. Pearson, "Rapid and sensitive protein similarity searches," *Science,* 227:1435–1441 (1985).

Matsuyama and Natori, "Purification of Three Antibacterial Proteins from the Culture Medium of NIH-Sape-4, an Embyronic Cell Line of *Sarcophaga peregrina,*" *J. Biol. Chem.* 263:17112–17116 (1988).

(List continued on next page.)

OTHER PUBLICATIONS

Matteucci and Caruthers, "Synthesis of Deoxyoligonucleotides on a Polymer Support", *J. Am. Chem. Soc.* 103:3185–3191 (1981).

Maxam et al., "Sequencing End-Labeled DNA with Base-Specific Chemical Cleavages", *Methods in Enzymology* 65:499–560 (1980).

Messing, et al., "A System for Shotgun DNA Sequencing", *Nucleic Acids Res.* 309–321 (1981).

Ouellette et al., "Developmental Regulation of Cryptdin, a Corticostatin/Defensin Precursor mRNA in Mouse Small Intestinal Crypt Epithelium," *J. Cell Biol.* 108:1687–1695 (1989).

Romeo et al., "Structure and Bactericidal Activity of an Antibiotic Dodecapeptide Purified from Bovine Neutrophils," *J. Biol. Chem.* 263:9573–9575 (1988).

Saiki, R. K., D. H. Gelfand et al., "Primer-directed enzymatic amplification of DNA with a Thermostable DNA polymerase," *Science,* 239:487–491 (1988).

Sanger et al., "DNA Sequencing with Chain-Terminating Inhibitors", *Proc. Natl. Acad. Sci.* (USA) 74:5463–5467 (1977).

Selsted et al., "Primary Structures of Three Human Neutrophil Defensins," *J. Clin. Invest.* 76:1436–1439 (1985).

Shaw et al., "A General Method for the Transfer of Cloned Genes to Plant Cells", *Gene* 23:315–330 (1983).

Shimatake and Rosenberg, "Purified λRegulatory Protein cII Positively Activates Promoters for Lysogenic Development", *Nature* 292:128–132 (1981).

Soravia et al., "Antimicrobial Properties of Peptides from Xenopus Granular Gland Secretions," *FEBS Lett.* 228:337–340 (1988).

Steiner et al., "Sequence and Specificity of Two Antibacterial Proteins Involved in Insect Immunity," *Nature* 292:246–248 (1981).

Stinchcomb et al., "Isolation and Characterisation of a Yeast Chromosomal Replicator", *Nature* 282:39–43 (1979).

Tsuchumper and Carbon, "Sequence of a Yeast DNA Fragment Containing a Chromosmal Replicator and the TRP1 Gene", *Gene* 10:157–166 (1980).

Van Solingen et al., "Fusion of Yeast Spheroplasts", *J. Bact.* 130:946–947 (1977).

Zasloff, "Magainins, a Class of Antimicrobial Peptides from Xenopus Skin: Isolation, Characterization of Two Active Forms, and Partial cDNA Sequence of a Precursor," *Proc. Natl. Acad. Sci. USA* 84:5449–5453 (1987).

Depicker et al., "Nopaline Synthase: Transcript Mapping and DNA Sequencing", *J. Mol. Appl. Gen.* 1:561–573 (1982).

Ouellette and Lualdi, "A Novel Mouse Gene Family Coding for Cationic, Cystene-rich Peptides", *J. Biol. Chem.* 265:9831–9837 (1990).

FIG. 2A

```
     asn pro val ser cys val arg asn lys gly ile cys val pro ile arg cys pro gly
1-    →   →   →   →   →   →   →   →   →   →   →   →   →   →   →   →   →   →   →
2-
```

FIG. 2B

```
5'                                              3'
  gaattcAAY CCH GTB AGI TGY GTT
        AAY CCH GTB TCY TGY GTT
```

FIG. 2C

```
5' AAC CCT GTC TCC TGT GTG CGC AAC AAG GGC ATC TGT GTG CCC AT
                                AAC AAG GGC ATC TGT GTG CCC ATC CGC TGC CCT GGC
```

FIG. 2D

```
5' AAT CCT GTA AGC TGT GTT AGG AAT AAA GGC ATC TGT GTG CCG ATC AGG TGT CCT GGA
```

FIG. 2A CONT'D ser met lys gln ile gly thr cys val gly arg ala val lys cys arg lys lys
--> --> --> --> --> --> --> --> --> --> --> --> --> --> --> --> --> -->

FIG. 2B CONT'D

5'
TAC TTY GTY TAD CCI TGDctcgag

FIG. 2C CONT'D

3'
TCC ATG AAG CAG ATT GG  3'

FIG. 2D CONT'D

AGC ATG AAA CAG ATT GGC ACC TGT GTT GGG CGG GCA GTA AAA TGC TGT AGA AAG AAG...3'

FIG. 3

```
CCGGCGCCCGCCGAGCCGCTCGGGACGCCAGC ATG AGG CTC CAT CAC CTG CTC    55
                                 Met Arg Leu His His Leu Leu      7

CTC GCG CTC CTC TTC CTG GTC CTG TCT GCT TGG TCA GGA TTT ACT CAA  103
Leu Ala Leu Leu Phe Leu Val Leu Ser Ala Trp Ser Gly Phe Thr Gln   23

GGA GTA GGA AAT CCT GTA AGC TGT GTT AGG AAT AAA GGC ATC TGT GTG  151
Gly Val Gly Asn Pro Val Ser Cys Val Arg Asn Lys Gly Ile Cys Val   39

CCG ATC AGG TGT CCT GGA AGC ATG AAA CAG ATT GGC ACC TGT GTT GGG  199
Pro Ile Arg Cys Pro Gly Ser Met Lys Gln Ile Gly Thr Cys Val Gly   39

CGG GCA GTA AAA TGC TGT AGA AAG AAG TAA AAGAAGGCCAAGACACAGCCGGG  252
Arg Ala Val Lys Cys Cys Arg Lys Lys End

ATCAATGCCCAGTCAGAAACTGCCCCTTTGACAGAGCGTCTAAAATTTAAACCAGAATAAAT  316
TTTGTTCAAAGTTAAAAAGTTAAAAAAAAAAAAAAAAAAA                         349
``` agcccaccaaccccctcagtccatgggactcaccaggcaagaacactggagcgggttgcca 60
tttccttcttcaaaaggaaccatcagtccagttc<u>agttcagttcagttcagtcgctcagt</u> 120
<u>ggtacccaactctttgcgacccccatgaattgcagcatgccaggactccctgtccatcacc</u> 180
<u>aactcccagagttcactcaaactcatgtccatcgagtcggtgatgccatccaaccatctc</u> 240
<u>atcctctgtcgccccttcttctcctgccccaaatccctcccagcaccagggtcttttcc</u> 300
<u>aatgagtcaactcttcgcatgaggtggccaaggtattggagcttcagcttcagcatgagt</u> 360
<u>ccttccaaagaacacccaggactgatctcctttaggatggactggttggatctccttgca</u> 420
<u>gtccaaaagactatcaagagtcttctccaacaccacagttcaaaagcatcaattctttgg</u> 480
<u>cgctcagcttcttcacagtccaactctcacatccatacatgaccactggaaaaaaccat</u> 540
<u>aggccttgactaggcggacctttgttggtaaagtaatatctctgcttttcaaatgctatc</u> 600
<u>taggttggtcataactttccttccaaggagtaatcgtgttttaatttcatggctgcaatc</u> 660
accatctgccatgattttggagccccaaaaataaagtctgacactgtttccactgtttcc 720
ccatctatttcccatgaagtgatgggatcatacgccattatcttagttttctgaatgttg 780
agctttaagccaacttttttcactctcatctttcactttcatcaagaggcttttagttcc 840
tcttcactttctgccatacgggtggtgtcatctgcatatttgaggttattgacatttctc 900
ccggcaatcttgattccagcttgtgcttcttccagccaataaggaactatagaaataaag 960
aaagtgaagtcacccagtcgtgtctgactctgtgcaatcccatgaactgtagcccaccag 1020
cctcctccatccatggaattttccaggcaagagtcctggagtggggtgccatttccttct 1080
gcacaggaaaacagtgggcactttcaaagccctggaagggcgaggggtggggctggagagc 1140
gggtaagcgaaggttcagcaagaagtctgtgccctgccagggaaacaggcaagtctgtgc 1200
cccttgccacacccctgcccatcagctgaactgactgccggaagaagcttcttgttaaaa 1260
gagcagcaggaaagcttttttct<span style="border:1px solid">ggggttttcc</span>ccagcctcattagcataagagtgactga 1320
ccctgaccctgctttgtgccataaaggccactcccatgacacacagggaagaggatcagt 1380
<span style="border:1px solid">taaccaatt</span>cctaataaccaaatccacagccagcccagaattcctcccggaacctgggac 1440
                                          +1
ctt<span style="border:1px solid">tataaa</span>gcggcaatcgcagtgtcttctccAGCATCAGCCGCAGAGCTCGGGACGCCA 1500
GCATGAGGCTCCATCACCTGCTCCTCGCGCTCCTCTTCCTGGTCCTGTCTGCTTGGTCAG 1560
  MetArgLeuHisHisLeuLeuLeuAlaLeuLeuPheLeuValLeuSerAlaTrpSerG
gtgagctcttgggagccctggagggagccgtgggctctctctcctgtttctacctccttc 1620
tgtcctgctaccccatctacacgtggtcagactaaacccaccatatttgatgctcctga 1680
gaagcctgcgctgagtccttagtagcgagaggggtctgagaagggccctgacaaattcct 1740

FIG. 8A

```
ggctgtttctaatccactctagtgagtccgagcttctgagcccatctcctcattggtttc      1800
atgaggaggaaacagaagatgtctctgttaagtgactcttattttttcttttttcataaa      1860
accaagaaatttgattttgtcccatgacagaagcacagaatgtcgctttataaatctttc      1920
tatccgaagggtagcggctctgggcaaccagagaagtccagaggtgagtcaggccaagcc      1980
tgggctttgggagctgcccttgggacactccgtgatgagtctcttcagcaggaaagtcct      2040
ccaggacacgtcgctgatgatgagaccctcgctccacagctgggaggcagcacatccaaa      2100
gcagtgtgcaggatcggctgtctgattttcatcttaccttgatatttccggaaatagga      2160
tgaaaatatgtaggaaggaaggagggagggagggagagagaggctgcagagactgagacc      2220
tgagacaactgattagatgtcaaaatcaagttgaaattcccttgtctgatcagtgttgtt      2280
tatgactgtaacccaactcttagcacagtggcagggagagaggacagggtgtaaggaaga      2340
cggcctctcagtgcctggggcctgggttcaatccctggagggggaactagagaaggacca      2400
gaggtgccttgtggccaaaagagaaaagggcctgtgaggaaggcccctggtcaggcatgt      2460
gagaggatgggaaggccgctgatcgggaggaaaccacaaagggaggaggagaggggctga      2520
ctggccccagtgctgagagtgttccgagttagtacagatgatgatacaaaacttttttt      2580
ctgaaccattgtcactgtcagctggtaagttgctttgagagtaagttctctttaaacagt      2640
tcttacactttcagctgcatcttttcctcctatctcagctctactacttgactgactcca      2700
tgagtcggaaaactaaacagtgaaaatagaccctgtgggccgcttctgactcctggcgg      2760
gaaggtggatgtagcagagcttcctggtctttgcccttgtggtggagctgaccccgcaca      2820
caaaccggggtcctcacaccccagtccctcagcctctggttctggaaacgtgagggtcca      2880
ccagagcctgggcagggtcaccgtctgtctgcaaactggtccacagggtcctggactcac      2940
atcttgttgtcacagaggccatgtccgcatctcatcacataaagccccagggccttgctc      3000
agaggggacacagctggccttctcgagatgctgctttcctgctgacacgttttccctct      3060
ctgttctcttttagGATTTACTCAAGGAGTAGGAAATCCTGTAAGCTGTGTTAGGAATA      3120
               lyPheThrGlnGlyValGlyAsnProValSerCysValArgAsnL
AAGGCATCTGTGTGCCGATCAGGTGTCCTGGAAGCATGAAACAGATTGGCACCTGTGTTG      3180
ysGlyIleCysValProIleArgCysProGlySerMetLysGlnIleGlyThrCysValG
GGCGGGCAGTAAAATGCTGTAGAAAGAAGTAAAAGAAGGCCAAGACACAGCCGGGATCAA      3240
lyArgAlaValLysCysCysArgLysLysEnd
TGCCCAGTCAGAAACTGCGCCCTTTGACAGAGCGTCTAAAATTTAAACCAGAATAAATTT      3300
TGTTCAAAGTTaaagaatcttgcccactggtcactgaggttgttgtgtggtgtctgatcc      3360
caaatgaattc
```

FIG. 8B

DNA ENCODING TRACHEAL ANTIMICROBIAL PEPTIDES

CROSS REFERENCE TO RELATED APPLICATIONS

This application is a continuation-in-part of U.S. Ser. No. 07/991,200 filed on Dec. 15, 1992, now abandoned, which is a continuation of Ser. No. 603,451 filed Oct. 25, 1990, now U.S. Pat. No. 5,202,420 which issued on Apr. 13, 1993.

FIELD OF THE INVENTION

The present invention relates generally to antimicrobial peptides referred to herein as tracheal antimicrobial peptides. More particularly, the present invention is related to a new class of polypeptides with antimicrobial activity, DNA and cDNA sequences encoding for the peptides, methods for the production and use thereof.

BACKGROUND OF THE INVENTION

The respiratory epithelium of mammals is a complex tissue responsible for numerous physiological functions, one of which is forming a key barrier to potentially harmful environmental threats. Multiple defense mechanisms have been identified which protect the respiratory tract from inhaled agents that are known to be responsible for airway disease, such as infectious agents, gases, and particulates. Newhouse, M. T. and J. Bienenstock, "Respiratory Tract Defense Mechanisms," *Textbook of Pulmonary Disease*, Little, Brown and Comp (1989). These multiple defenses are the result of a combination of anatomical design of the airway, together with the physiological role of local and circulating cells.

Recent isolation and characterization of antimicrobial peptides in a variety of species and tissues has unveiled a new component of animal host defense. These various peptides, which can be classified into families based on common sequences, secondary structure and/or sites of activity, are believed to participate in defense against potential microbiological pathogens. Cecropins were the first well characterized family of structurally related antimicrobial peptides and are found in a wide distribution of insects. Boman, H. G. and D. Hultmark, *Ann. Rev. Microbiol.*, 41:103–126 (1987). They are coordinately expressed in the fat body of insect larvae following infection or injury. In vertebrates, the magainin family of antimicrobial peptides have been isolated from glands of the skin and gastrointestinal tract of *Xenopus laevis*, and are thought to form the basis for a defense system of the amphibian mucosal surfaces against infection. Soravia, E., G. Martini et al., "Antimicrobial properties of peptides from Xenopus granular gland secretions," *FEBS Lett.*, 228:337–40 (1988); Zasloff, M. A., "Magainins, a class of antimicrobial peptides from Xenopus skin: Isolation, characterization of two active forms, and partial cDNA sequence of a precursor," *Proc Natl Acad Sci USA*, 84:5449–53 (1987). Defensins are peptides found in phagocytic cells isolated from several mammalian species including man, and may be characterized by eight invariant residues within the sequence. Gabay, J. E., "Microbicidal mechanisms of phagocytes," *Curr Opin Immunol,* 1(1):36–40 (1988); Gabay, J. E., R. W. Scott et al., "Antibiotic proteins of human polymorphonuclear leukocytes," *Proc Natl Acad Sci USA,* 86 (14):5610–4 (1989); Ganz, T., "Extracellular release of antimicrobial defensins by human polymorphonuclear leukocytes," *Infect Immun,* 55(3):568–71 (1987); Ganz, T., J. A. Metcalf et al., "Microbicidal/cytotoxic proteins of neutrophils are deficient in two disorders: Chediak-Higashi syndrome and 'specific' granule deficiency," *J Clin Invest,* 82 (2):552–6 (1988); Ganz, T., J. R. Rayner et al., "The structure of the rabbit macrophage defensin genes and their organ-specific expression," *J Immunol,* 143 (4):1358–65 (1989); Ganz, T., M. E. Selsted et al., "Antimicrobial activity of phagocyte granule proteins," *Semin Respir Infect,* 1 (2) :107–17 (1986); Ganz, T., M. E. Selsted et al., "Defensins," *Eur J Haematol,* 44 (1) :1–8 (1990a); Ganz, T., M. E. Selsted et al., "Defensins," *Eur J Haematol,* 44 (1):1–8 (1990b); Ganz, T., M. E. Selsted et al., "Defensins. Natural peptide antibodies of human neutrophils," *J Clin Invest,* 76 (4):1427–35 (1985). They possess antimicrobial activity in vitro against bacteria, fungi, and viruses, and may contribute to the "oxygen-independent" defense pathways of these cells. Lehrer, R. I., T. Ganz et al., "Oxygen-independent bactericidal systems. Mechanisms and disorders," *Hematol Oncol Clin North Am,* 2 (1):159–69 (1988). Expression of defensin in a non-myeloid tissue source, the mouse small intestinal crypt cells, has also been reported. Ouellette, A. J., R. M. Greco et al., "Developmental regulation of cryptdin, a corticostatin/defensin precursor mRNA in mouse small intestinal crypt epithelium," *J Cell Biol,* 108 (5):1687–95 (1989).

Cecropins, magainins, and defensins all share the properties of being cationic and membrane active, and evidence suggests that their antimicrobial activity is secondary to their ability to selectively disrupt membranes, possibly by channel formation. Bevins, C. L. and M. A. Zasloff, "Peptides from frog skin," *Ann. Rev. Biochem.,* 59:395–414 (1990); Kagan, B. L., M. E. Selsted et al., "Antimicrobial defensin peptides form voltage-dependent ion-permeable channels in planar lipid bilayer membranes," *Proc Natl Acad Sci USA,* 87 (1):210–4 (1990); Lehrer, R. I., A. Barton et al., "Interaction of human defensins with *Escherichia coli*. Mechanism of bactericidal activity," *J Clin Invest,* 84 (2):553–61 (1989); Zasloff, M. A., "Magainins, a class of antimicrobial peptides from Xenopus skin: Isolation, characterization of two active froma, and partial cDNA sequence of a precursor," *Proc Natl Acad Sci USA,* 84:5449–53 (1987).

These newly emerging family of basic, cysteine-rich peptides with antimicrobial activity found throughout the animal kingdom include the defensins (Ganz, T., M. E. Selsted et al , "Defensins, " *Eur J Haematol* 44 (1): 1–8 (1990b)), insect defensins (Lambert, J., E. Keppi et al., "Insect immunity:isolation from immune blood of the dipteran Phormia terranovae of two insect antibacterial peptides with sequence homology to rabbit lung macrophage bactericidal peptides" [published erratum appears in Proc Natl Acad Sci USA May;86 (9):3321 (1989)]. *Proc Natl Acad Sci USA* 86 (1): 262–6 (1989)), bactenecins (Romeo D., B. Skerlavaj et al ,. "Structure and bactericidal activity of an antibiotic dodecapeptide purified from bovine neutrophils," *J Biol Chem,* 263:9573–75 (1988)), sapecins (Matsuyama, K. and Natori, S. "Purification of three antibacterial proteins from the culture medium of NIH-Sape-4, an embryonic cell line of *Sarcophaga peregrina*," *J Biol Chem,* 263:17112–16 (1988)) and royalisin (Fujiwara, S., J. Imai et al., "A potent antimicrobial protein in royal Jelly, " *J Biol Chem,* 265: 11333–37 (1990)) Defensins are basic peptides of 30 to 34 amino acids with 3 disulfide bonds. The known characterized defensins from both myeloid and non-myeloid tissues all have highly conserved amino aced residues within the family, including 6 invariant cysteines. Aside from a pair of cysteine residues near the carboxy-terminus of the tracheal antimicrobial peptide of this invention, no consensus or other residues are shared between these peptides. Furthermore, the 5' region of all known defensin cDNAs are strikingly conserved even across species, and no similarity with this consensus region is found in the tracheal antibiotic peptide's cDNA. Comparison with the other cysteine containing antimicrobial peptides shows no similarity.

Formal searches of the NRBF protein data base using a modification (IBI) of fastP, Lipmann, D. J. and W. R. Pearson, "Rapid and sensitive protein similarity searches," *Science*, 227: 1435–41 (1985) and the Intelligenetics Search found no protein sequences that disclose the tracheal antimicrobial peptides of the instant invention. A nucleotide-based search of the GenBank data base using the University of Wisconsin Genetics analysis software, Devereux, J., P. Haeberli et al., "A comprehensive set of sequence analysis programs for the VAX, " *Nucl. Acids Res.*, 12:387–95 (1984), was similarly unrevealing.

SUMMARY OF THE INVENTION

There is provided by this invention a novel tracheal antimicrobial peptide (TAP) and a novel precursor of TAP.

There is provided by this invention a novel cDNA coding for a TAP and a novel cDNA coding for a TAP precursor.

There is provided by this invention a novel protein produced from the cDNA coding for a TAP and a novel protein produced from the cDNA coding for a TAP precursor.

There is provided by this invention a novel protein produced from the DNA coding for a TAP.

There is provided by this invention a novel substantially purified, isolated mammalian TAP precursor comprising a protein having at least in part or in whole substantially the same amino acid sequence as the protein defined in SEQ ID NO:3.

There is provided by the invention a substantially purified, isolated mammalian TAP comprising a protein having at least in part or in whole substantially the same amino acid sequence and at least the same antimicrobial activity as the protein defined in SEQ ID NO:1.

There are provided novel methods of use and diagnosis for TAP, cDNA coding for TAP and DNA coding for TAP.

There are provided novel recombinant host cells transformed with DNA coding for TAP or a portion thereof sufficient for the expression of TAP by said host cells.

There is provided a novel method of producing TAP which comprises culturing recombinant host cells wherein a recombinant DNA transformed in said host cell has a DNA sequence encoding TAP, operably linked to appropriate regulatory control sequences which are capable of effecting the expression of said coding sequences in said transformed cells.

There is provided a novel recombinant vector capable of expression in a suitable expression system which comprises a DNA sequence encoding TAP operably linked to control sequences compatible with said expression system.

Applicants have found that the ciliated respiratory mucosa of mammals contains peptide-based antimicrobial activity, to complement other defense systems of the airway. An abundant novel peptide found in extracts of the mammalian tracheal mucosa, is isolated herein on the basis of potent antimicrobial activity. This molecule is hereinafter referred to as tracheal antimicrobial peptide (TAP).

BRIEF DESCRIPTION OF THE DRAWINGS

FIG. 1 Purification of the antimicrobial peptide from Bovine trachea:

FIG. 2. Amino acid sequence of TAP and related nucleotide sequences:

FIG. 2A. Amino acid sequence (SEQ ID NO:1) of a TAP based on a combination of peptide amino acid sequence analysis, mass spectral analysis, and cDNA sequence analysis. The arrows indicate the results from Edman degradation analysis: sequence 1 is from direct amino-terminal analysis, sequence 2 is following cyanogen bromide cleavage and HPLC purification. Cysteine residue were determined following reduction and treatment with 4-vinylpyridine.

FIG. 2B. Nucleotide sequences (SEQ ID NO:6, SEQ ID NO:7 and SEQ ID NO:12) of degenerate oligonucleotides used for PCR amplification. A 1:1 mixture of oligonucleotides was used as an upstream primer. Abbreviations used: Y=C,T; R=A,G; D=G,A,T; B=C,G,T. Lower case letters denote 5' flanking sequences included in the oligonucleotide to aid subcloning.

FIG. 2C. Nucleotide sequence of oligonucleotides (SEQ ID NO:8 and SEQ ID NO:9) used in cDNA screening. Selection of sequence was based on partial peptide sequence and codon usage tables.

FIG. 2D. Partial nucleotide sequence (SEQ ID NO:2) of bovine TAP cDNA obtained from dideoxysequence analysis.

FIG. 3. Nucleotide sequence (SEQ ID NO:4) and predicted amino acid sequence (SEQ ID NO:3) of a TAP precursor. Amino acid numbering starts with the initiation codon. The mature peptide (SEQ ID NO:1) beginning at residue 27 is underlined. The polyadenylation signal is boxed.

FIG. 5. Northern blot analysis of TAP RNA.

FIG. 6. In situ hybridization of TAP mRNA expression in airway tissue.

Ar represents arteriole (panel A-C) or small artery (panel D); a represents alveolus; L represents lumen. Bar equals 25 microns.

Figures 7A, 7B:
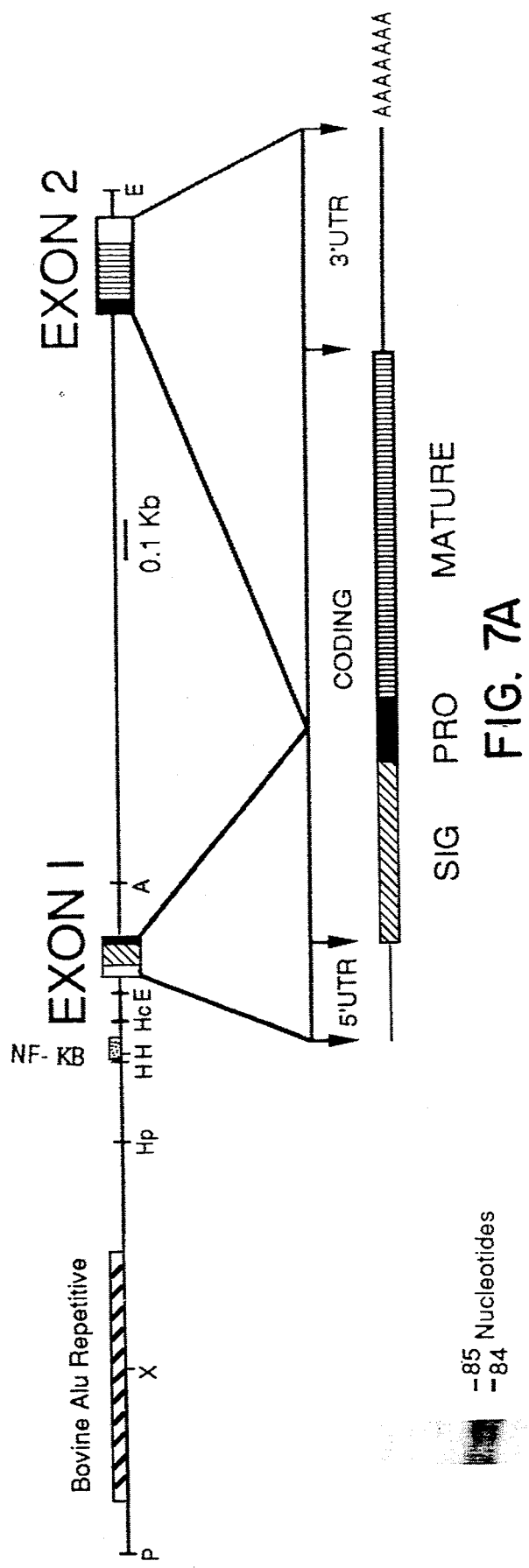

FIG. 7A. Analysis of the bovine TAP gene.

FIG. 7A shows a restriction map of the bovine TAP gene, including 1.4 kB of upstream sequence. A, ApaI; H, Hindiii; E, EcoRI; Hc, Hinc2; Hp, Hpa2; P, Pst 1; X, Xho 1. The structure of the cDNA and the predicted precursor structure of TAP deduced from the cDNA sequence is also shown.

FIG. 7B shows primer extensions of TAP mRNA using TAP48A as an oligonucleotide primer. The bands correspond to 84 and 85 nucleotides in length.

FIG. 8A and FIG. 8B provide the nucleotide sequence of the TAP gene. Exons are represented by uppercase letters. The sequence homologous to the bovine repititive elements is underlined. TATA box, CAAT box, and NFkB sequences are boxed.

FIG. 9. Southern blot analysis of the TAP-related sequences. Bovine genomic DNA was digested with Eco R1 or Taq 1 restriction endonuclease as indicated, and size fractionated by agarose gel electrophoresis. The DNA was transferred to nitrocellulose membrane and hybridized with one of the following $^{32}$P-end labelled oligonucleotide.

Figure 9A:
Figure 9B:
Figure 9C:

FIG. 9A oligonucleotide TAP48A
FIG. 9B oligonucleotide TAP160A
FIG. 9C oligonucleotide TAP118S

DETAILED DESCRIPTION OF THE INVENTION

The term "antimicrobial" as used herein refers to killing microorganisms or suppressing their multiplication and growth.

As used herein, "TAP" refers to a protein having at least in part or in whole substantially the same amino acid sequence and at least the same antimicrobial activity as the protein defined in SEQ ID NO:1. Said antimicrobial activity being defined as substantially preventing the growth of E. coli K12 strain D31 under the conditions described below (TableII) at a concentration of at least 100 μg/ml TAP. For convenience, a protein having at least in part or in whole substantially the same amino acid sequence as the protein defined in SEQUENCE ID NO:3 is hereinafter referred to as a TAP precursor.

The TAP protein of the invention, depending on the pH of its environment, if suspended or in solution, or of its environment when crystallized or precipitated, if in solid form, may be in the form of pharmaceutically acceptable salts or may be in neutral form. The free amino groups of the protein are, of course, capable of forming acid addition salts with, for example, inorganic acids such as hydrochloric, phosphoric, or sulfuric acid; or with organic acids such as, for example, acetic, glycolic, succinic, or mandelic acid. The free carboxyl groups are capable of forming salts with bases, including inorganic bases such as sodium, potassium, or calcium hydroxides, and such organic bases as piperidine, glucosamine, trimethylamine, choline, and caffeine. In addition, the protein may be modified by combination with other biological materials such as lipids and saccharides, or by side chain modification such as acetylation of amino groups, phosphorylation of hydroxyl side chains, or oxidation of sulfhydryl groups.

Modifications of TAP are included within the scope of the definition, so long as the antimicrobial activity as described herein is retained. Finally, it is understood that minor modifications of TAP may result in proteins which have substantially equivalent or enhanced antimicrobial activity as compared to the sequence set forth in SEQ ID NO:1. These modifications may be deliberate, as through site-directed mutagenesis, or may be accidental such as through mutation in hosts which are TAP producers. All of these modifications are included as long as the antimicrobial activity, is retained.

Acid extracts of mammalian tracheal mucosa, e.g. bovine, have been found to have the peptide TAP, in abundant quantities, a peptide with potent antimicrobial activity (FIG. 1). A mammalian TAP (SEQ ID NO:1) was isolated by a combination of size-exclusion (FIG. 1A), ion-exchange (FIG. 1C), and reverse-phase (FIG. 1D) chromatographic fractionations using antimicrobial activity against a strain of E. coli as a functional assay. Purity of the isolated peptide (SEQ ID NO:1) was >95% as determined by a combination of analytical reverse-phase and capillary-gel electrophoresis (data not shown). The yield of the isolated material was 2 μg/g of wet tracheal mucosa.

The mammalian TAP, SEQ ID NO:1, was characterized by amino acid sequence (data not shown), and compositional analysis (Table I) Mass spectral analysis determined the molecular weight of the peptide (SEQ ID NO:1) to be 4085 Da.

A cDNA (SEQ ID NO:4) corresponding to the precursor peptide, was cloned (FIG. 3), and contains an open reading frame of 64 amino acids (SEQ ID NO:3). It is believed that the thirty-eight carboxy-terminal residues of this open reading frame correspond to the isolated peptide (SEQ ID NO:1) based on several observations. First, the 33 amino acids determined from the amino acid sequence data align perfectly with residues 26–59 of the deduced sequence (FIG. 2A (SEQ ID NO:1) v. FIG. 2D (SEQ ID NO:2)). Second, the amino acid composition agrees favorably with the deduced amino acid sequence (Table I). Finally, the observed molecular weight of the isolated protein (SEQ ID NO:1), 4085 Da is in complete agreement with the deduced sequence, assuming the six cysteine residues all participate in intramolecular disulfide bonds. The predicted pI is 13.0, and there are no aromatic residues, both of which are consistent with the observed protein data.

Figure 5A:
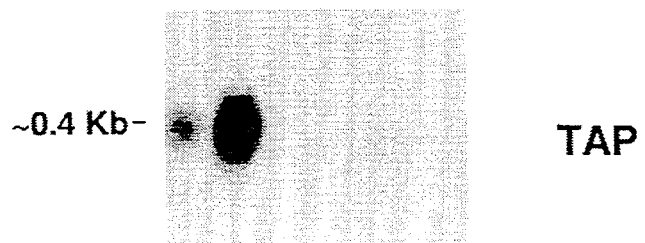
FIG. 5A Tissue distribution of TAP mRNA. Lane 1, nasal septum. Lane 2, tracheal mucosa. Lane 3, fallopian tube. Lane 4, small intestine. Lane 5, fetal trachea (approximately 4 months gestation). Lane 6, fetal trachea (approximately 6 months gestation).
Figure 5B:
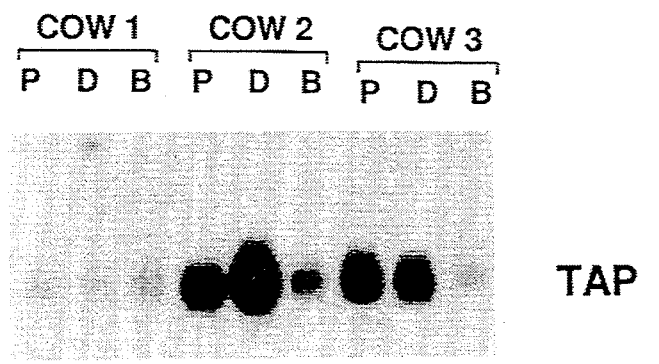
FIG. 5B. Distribution of TAP mRNA along the airway from three independent cows (cow 1, cow 2, cow 3). P, proximal tracheal mucosa; D, distal tracheal mucosa; B, bronchiolar tissue.
Figure 6B:
FIG. 6B. Light field photomicrograph of cross section of bovine bronchiolar tissue hybridized with $^{35}$S-labeled with sense probe TAP113S and stained with hematoxylin and eosin.
Figure 6D:
FIG. 6D. Light field photomicrograph of cross section of bovine lung tissue hybridized with 35S-labeled antisense probe TAP160A and stained with hematoxylin and eosin.
Figure 6A:
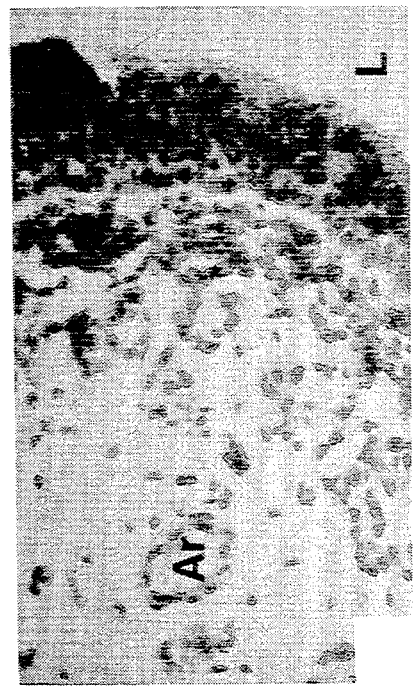
FIG. 6A. Light field photomicrograph of cross section of bovine bronchiolar tissue hybridized with $^{35}$S-labeled with antisense probe TAP160A and stained with hematoxylin and eosin.

The TAP gene, SEQ ID NO: 5, is expressed primarily in the columnar epithelial cells of the mucosa lining the bovine airway. RNA analysis indicates that TAP is expressed along the entire length of the conducting airway, from nasal to bronchiolar tissue (FIG. 5), and can be further localized to the more apical aspect of the pseudostratified epithelium (FIG. 6A). No expression was observed in non-airway tissue. The TAP gene has two exons, similar to a human epithelial defensin gene (4).

The TAP gene includes a consensus sequence for an NFKB recognition site 181 bases upstream from the transcriptional start site. NFKB has been shown to enhance the expression of a variety of genes involved in immune and inflammatory responses, and can be modulated by lipopolysaccharides (LPS) and phorbol esters (16). Lenardo, M. J. and Baltmore, D., (1990) Cell 58, 227–229.

When assayed in vitro against several different strains of microbes, including some which are respiratory pathogens, a mammalian TAP (SEQ ID NO:1) of bovine origin showed similar inhibitory activity to that of synthetic magainin 2-NH$_2$ (SEQ ID NO:6), a naturally occurring antibiotic peptide from frog skin. See TableII. While TAP (SEQ ID NO:1) was most active against E. coli and K. pneumonia, significant antimicrobial activity was also seen when applied to C. albicans, thus TAP's spectrum of activity is believed to span at least to both bacteria and fungi.

Having described the amino acid sequence of a TAP (SEQ ID NO:1), including the precursor peptide (SEQ ID NO:3), it is believed these polypeptides can be routinely synthesized in substantially pure form by standard techniques well known in the art, such as commercially available peptide synthesizers and the like.

Additionally, it is believed TAP can be efficiently prepared using any of numerous well known recombinant techniques such as those described in U.S. Pat. No. 4,677,063 which patent is incorporated by reference as if fully set forth herein. Briefly, most of the techniques which are used to transform cells, construct vectors, extract messenger RNA, prepare cDNA libraries, and the like are widely practiced in the art, and most practitioners are familiar with the standard resource materials which describe specific conditions and procedures. However, for convenience, the following paragraphs may serve as a guideline.

Procaryotes most frequently are represented by various strains of E. coli. However, other microbial strains may also be used, such as bacilli, for example Bacillus subtilis, various species of Pseudomonas, or other bacterial strains. In such procaryotic systems, plasmid vectors which contain replication sites and control sequences derived from a species compatible with the host are used. For example, E. coli is typically transformed using derivatives of pBR322, a plasmid derived from an E. coli species by Bolivar, et al, Gene (1977) 2:95. pBR322 contains genes for ampicillin and tetracycline resistance, and thus provides additional markers which can be either retained or destroyed in constructing the desired vector. Commonly used procaryotic control sequences include promoters for transcription initiation, optionally with an operator, along with ribosome binding site sequences, include such commonly used promoters as the beta-lactamase (penicillinase) and lactose (lac) promoter systems (Chang, et al., Nature (1977) 198:1056) and the tryptophan (trp) promoter system (Goeddel, et al. Nucleic Acids Res (1980) 8:4057) and the lambda derived P$_L$ promoter and N-gene ribosome binding site (Shimatake, et al., Nature (1981) 292:128).

In addition to bacteria, eucaryotic microbes, such as yeast, may also be used as hosts. Laboratory strains of Saccharomyces cerevisiae, Baker's yeast, are most used although a number of other strains are commonly available. While vectors employing the 2 micron origin of replication are illustrated, Broach, J. R., Meth Enz (1983) 101:307, other plasmid vectors suitable for yeast expression are known (see, for example, Stinchcomb, et al., Nature (1979) 282:39, Tschempe, et al., Gene (1980)10:157 and Clark, L., et al., Meth Enz (1983) 101:300). Control sequences for yeast vectors include promoters for the synthesis of glycolytic enzymes (Hess, et al., J Adv Enzyme Req (1968) 7:149; Holland, et al. Biochemistry (1978) 17:4900). Additional promoters known in the art include the promoter for 3-phosphoglycerate kinase (Hitzeman, et al., J Biol Chem (1980) 255:2073), and those for other glycolytic enzymes such as glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters, which have the additional advantage of transcription controlled by growth conditions are the promoter regions for alcohol dehydrogenase 2, isocytochrome C, acidphosphatase, degradative enzymes associated with nitrogen metabolism, and enzymes responsible for maltose and galactose utilization (Holland, ibid). It is also believed terminator sequences are desirable at the 3' end of the coding sequences. Such terminators are found in the 3' untranslated region following the coding sequences in yeast-derived genes. Many of the vectors illustrated contain control sequences derived from the enolase gene containing plasmid peno46 (Holland, M. J., et al., J Biol Chem (1981) 256:1385) or the LEU2 gene obtained from YEp13 (Broach, J., et al., Gene (1978) 8:121), however any vector containing a yeast compatible promoter, origin of replication and other control sequences is suitable.

It is also, of course, possible to express genes encoding polypeptides in eucaryotic host cell cultures derived from multicellular organisms. See, for example, Tissue Cultures, Academic Press, Cruz and Patterson, editors (1973). Useful host cell lines include VERO, HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) Fiers, et al., Nature (1978) 273:113), or other viral promoters such as those derived from polyoma, Adenovirus 2, bovine papilloma virus, or avian sarcoma viruses. General aspects of mammalian cell host system transformations have been described e.g. by Axel; U.S. Pat. No. 4,399,216. It now appears, also that "enhancer" regions are important in optimizing expression; these are, generally, sequences found upstream or downstream of the promoter region in non-coding DNA regions. Origins of replication may be obtained, if needed, from viral sources. However, integration into the chromosome is a common mechanism for DNA replication in eucaryotes. Plant cells are also now available as hosts, and control sequences compatible with plant cells such as the nopaline synthase promoter and polyadenylation signal sequences (Depicker, A., et al., *J Mol Appl Gen* (1982) 1:561) are available.

Depending on the host cell used, transformation is done using standard techniques appropriate to such cells. The calcium treatment employing calcium chloride, as described by Cohen, S. N., *Proc Natl Acad Sci (USA)* (1972) 69:2110, or methods described in Molecular Cloning: *A Laboratory Manual* (1988) Cold Spring Harbor Press, could be used for procaryotes or other cells which contain substantial cell wall barriers. Infection with *Agrobacterium tumefaciens* (Shaw, C. H., et al., *Gene* (1983) 23:315) is believed useful for certain plant cells. For mammalian cells without such cell walls, the calcium phosphate precipitation method of Graham and van der Eb, *Virology* (1978) 52:546 can be used. Transformations into yeast can be carried out according to the method of Van Solingen, P., et al., *J Bact* (1977) 130:946 and Hsiao, C. L., et al., *Broc Natl Acad Sci (USA)* (1979) 76:3829.

cDNA or genomic libraries can be screened using the colony hybridization procedure. Generally, each microtiter plate is replicated onto duplicate nitrocellulose filter papers (S&S type BA-85) and colonies are allowed to grow at 37° C. for 14–16 hr on L agar containing 50 μg/ml Amp. The colonies are lysed and DNA fixed to the filter by sequential treatment for 5 min with 500 mM NaOH, 1.5M NaCl, and are washed twice for 5 min each time with 5×standard saline citrate (SSC). Filters are air dried and baked at 80° C. for 2 hr. The duplicate filters are prehybridized at 42° C. for 6–8 hr with 10 ml per filter of DNA hybridization buffer (5×SSC, pH 7.0 5×Denhardt's solution (polyvinylpyrrolidine, plus Ficoll and bovine serum albumin; 1x=0.02% of each), 50 mM sodium phosphate buffer at pH 7.0, 0.2% SDS, 20 μg/ml Poly U, and 50 μg/ml denatured salmon sperm DNA).

The samples can be hybridized with kinased probe under conditions which depend on the stringency desired. Typical moderately stringent conditions employ a temperature of 42° C. for 24–36 hr with 1–5 ml/filter of DNA hybridization buffer containing probe. For higher stringencies high temperatures and shorter times are employed. Generally, the filters are washed four times for 30 min each time at 37° C. with 2SSC, 0.2% SDS and 50 mM sodium phosphate buffer at pH 7, then are washed twice with 2SSC and 0.2% SDS, air dried, and autoradiographed at −70° C. for 2 to 3 days.

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

Site specific DNA cleavage can be performed by treating the DNA with a suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 μg of plasmid or DNA sequence is cleaved by one unit of enzyme in about 20 μl of buffer solution. Incubation times of about one hour to two hours at about 37° C. are workable, although variations can be tolerated. After each incubation, protein can be removed by extraction with phenol/chloroform, and may be followed by ether extraction, and the nucleic acid recovered from aqueous fractions by precipitation with ethanol followed by running over a Sephadex G-5 spin column. If desired, size separation of the cleaved fragments may be performed by polyacrylamide gel or agarose gel electrophoresis using standard techniques. A general description of size separations can be found in Methods in Enzymology (1980) 65:499–560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6 mM $MgCl_2$, 6 mM DTT and 5–10 μM dNTPs. The Klenow fragment fills in at 5′ sticky ends but chews back protruding 3′ single strands, even though the four dNTPs are present. If desired, selective repair can be performed by supplying only one of the, or selected, dNTPs within the limitations dictated by the nature of the sticky ends. After treatment with Klenow, the mixture is extracted with phenol/chloroform and ethanol precipitated followed by running over a Sephadex G-50 spin column. Treatment under appropriate conditions with S1 nuclease results in hydrolysis of any single-stranded portion.

Synthetic oligonucleotides can be prepared by the triester method of Metteucci, et al. (*J Am Chem Soc* (1981) 103:3185) or using commercially available automated oligonucleotide synthesizers. Kinasing of single strands prior to annealing or for labeling is achieved using an excess, e.g., approximately 10 units of polynucleotide kinase to 0.1 nmole substrate in the presence of 50 mM Tris, pH 7.6, 10 mM $MgCl_2$, 5 mM dithiothreitol, 1–2 Mm ATP, 1.7 pmoles $\gamma^{32}P$-ATP (2.9 mCi/mmole), 0.1 mM spermidine, 0.1 mM EDTA.

Ligations can be performed in 15–30 μl volumes under the following standard conditions and temperatures: 20 mM Tris-Cl pH 7.5, 10 mM $MgCl_2$, 10 mM DTT, 33 μg/ml GSA, 10 mM-50 mM NaCl, and either 40 μM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 μg/ml total DNA concentrations (5–100 nM total end concentration). Intermolecular blunt end ligations (usually employing a 10–30 fold molar excess of linkers) are performed at 1 μM total ends concentration.

In vector construction employing "vector fragments", the vector fragment can be treated with bacterial alkaline phosphatase (BAP) in order to remove the 5′ phosphate and prevent religation of the vector. BAP digestions can be conducted at pH 8 in approximately 150 mM Tris, in the presence of Na+ and Mg+2 using about 1 unit of BAP per μg of vector at 60° C. for about one hour. In order to recover the nucleic acid fragments, the preparation is extracted with phenol/chloroform and ethanol precipitated and desalted by application to a Sephadex G-50 spin column. Alternatively, religation can be prevented in vectors which have been double digested by additional restriction enzyme digestion of the unwanted fragments.

For portions of vectors derived from cDNA or genomic DNA which require sequence modifications, site specific primer directed mutagenesis can be used. This is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques can be hybridized with kinased synthetic primer at a temperature which permits hybridization of an exact match, but at which the mismatches with the original strand are sufficient to prevent hybridization. Plaques which hybridize with the probe are then picked, cultured, and the DNA recovered.

Correct ligations for plasmid construction can be confirmed by first transforming a suitable host with the ligation mixture. Successful transformants are selected by ampicillin, tetracycline or other antibiotic resistance or using other markers depending on the mode of plasmid construction, as is understood in the art. Plasmids from the transformants can then be prepared according to the method of Clewell, D. B., et al. *Proc Natl Acad Sci* (USA) (1969) 62:1159, optionally following chloramphenicol amplification (Clewell, D. B., *J Bacteriol* (1972) 110:667). The isolated DNA is analyzed by restriction and/or sequenced by the dideoxy method of Sanger, F., et al. *Proc Natl Acad Sci (USA)* (1977) 74:5463 as further described by Messing, et al., F. Supp. *Nucleic Acids Res* (1981) 9,309, or by the method of Maxam, et al., *Methods in Enzymology* (1980) 65:499.

In a third alternative, TAP can be prepared directly from a mammalian trachea as described below.

Also provided by this invention are methods of treating a microbial infection, such as bacterial or fungal, comprising administering to a mammal in need of such treatment an antimicrobially effective amount of TAP. Such treatment can be systemic or topical for treatment of e.g. acne, burns, eye infections, mouthwash, deodorant or topical fungicide. TAP could also be used as a contact disinfectant.

For use as an antimicrobial agent, TAP can be formulated into pharmacological compositions containing an effective amount of TAP and a usual nontoxic carrier, such carriers being known to those skilled in the art. The composition can be given via a route of administration suited to the form of the composition. Such compositions are, for example, in the form of usual liquid preparations including solutions, suspensions, emulsions and the like which can be given orally, intravenously, subcutaneously or intramuscularly. The composition can be administered in an antimicrobially effective amount, generally a dose of about 0.1 to about 100 mg/kg/day, calculated as protein is expected to be useful.

Other utilities of the invention disclosed herein include, use of the cDNA sequence of TAP as a marker for various genetic studies in the mammal. This type of marker can be used to diagnose genetic diseases which may be linked to this marker, if not directly due to a defect in the TAP gene. In addition, genetic markers such as this can be used in Restriction Fragment Length Polymorphism (RFLP) studies for breeding purposes as are other genetic markers.

Additionally, since TAP is found in the mammalian airway and may represent part of the host defense against infections, it is believed that overexpression of TAP is induced by the presence of certain microbes. Therefore, the presence of higher quantities of TAP may indicate the presence of specific organisms or the beginning of an infectious state. Quantitation of TAP protein by immunoassay or other such methods well known in the art, or measurement of TAP messenger RNA by well known hybridization techniques may serve as a diagnostic tool for infections.

MATERIAL AND METHODS

EXAMPLE 1

General Methodology All reagents were standard reagent grade from Baker, Philipsburg, N.J. or Fisher, Pittsburg, Pa. unless otherwise noted. All bacteriological media were from Difco, Detroit, Mich. Restriction enzymes were purchased from Bethesda Research Laboratories (Gaithersburg, Md.) and were used according to manufacturer's protocol. Oligonucleotide probes were end labelled to a specific activity of ca. $10^7$ DPM/pmol using gamma-[$^{32}$P]dCTP (3000Ci/mmol, DuPont, Wilmington, Del.) and T4 polynucleotide kinase (Stratagene, LaJolla, Calif.). Double-stranded DNA probes were labelled to a specific activity of ca. $10^9$ CPM/μg using alpha-[$^{32}$P]dCTP (800 Ci/mmol), (DuPont, Wilmington, Del.) and T7 DNA polymerase with random oligonucleotide primers (Stratagene). Purified plasmid DNA was sequenced using the dideoxy-termination method with T7 DNA polymerase (U.S. Biochemicals).

EXAMPLE 2

Tissue. A segment of adult bovine trachea (just proximal to the carina and approximately 40 cm in length) was obtained fresh from a local meat processing plant. The tissue was immediately placed on wet ice and processed within 2-3 hours. Preliminary experiments indicated that immediate processing of tissue gave no significant further improvement in yield. The epithelium and adherent connective tissue, dissected on ice from the underlying connective tissue and cartilage, was placed immediately in liquid nitrogen. The frozen tissue was then stored at $-70°$ C. for periods up to several months before further processing.

EXAMPLE 3

Protein Isolation. The frozen tracheal epithelium was pulverized with a mortar and pestle under liquid nitrogen. The frozen tissue powder was placed in boiling 10% (v/v) acetic acid, and boiling was continued for 10 minutes. The solution was allowed to cool to room temperature, and centrifuged at 23,000× g. for 30 minutes at 10° C. The resulting supernatant was divided into 30 ml aliquots and each aliquot was applied to a C18 Sep-Pak cartridge (Millipore Corp., Bedford, Mass.). This, and all subsequent procedures were performed at room temperature. The cartridges were washed with 0.1% trifluoroacetic acid (TFA) in $H_2O$ (Buffer C) and then eluted with 4 ml of acetonitrile/0.1% TFA (60:40, v/v; Buffer D). The cartridge eluates were dried, resuspended in 1-2 ml 6M guanidinium-HCl/20mM Tris-HCl, pH 7.4. The solution was applied to a Biogel P-30 column (40 cm×2.5 cm diameter, Bio Rad) which had been pre-equilibrated with 50mM ammonium formate, pH 4.1. The exclusion limit was 40 kDa. The column was developed with the same ammonium formate buffer, and each fraction (2 ml) was lyophilized, resuspended in water (0.1 ml) and assayed for antimicrobial activity as described. Zasloff, M. A., "Magainins, a class of antimicrobial peptides from Xenopus skin: Isolation, characterization of two active forms, and partial cDNA sequence of a precursor," *Proc Natl Acad Sci USA*, 84:5449–53 (1987). The active fractions were pooled, and applied to a sulfoethyl ion exchange HPLC column (Poly LC, Columbia, Md.). A 45 minute linear elution-gradient from buffer A to buffer B was employed at a flow rate of 1 ml./min. Buffer A contained 25% acetonitrile/5 mM potassium phosphate, pH 5.3, and buffer B was identical to buffer A except that it also contained 1 M NaCl. Preliminary experiments had established that only a fraction eluting at 26 minutes contained significant antimicrobial activity. In subsequent isolations, this fraction was applied to a reverse-phase HPLC column and fractionated using a linear gradient buffer C to buffer D at 1 ml./min. The peak fraction eluting at 28.5 minutes was lyophilized and resuspended in $H_2O$ at an approximate concentration of 0.5 mg/ml.

EXAMPLE 4

Protein Sequence Analysis. The isolated peptide was subjected to amino acid analysis using an amino acid analyzer with automated hydrolysis (Applied Biosystems model 420, ABS, Foster City, Calif.). Sequence analysis was determined by the Edman degradation method on a pulsed liquid phase sequencer (Applied Biosystems model 477A, ABS). Cysteine residues were identified by sulfhydryl reduction followed by reaction with 4-vinylpyridine, Selsted M. E., S. S. Harwig et al., "Primary structures of three human neutrophil defensins," *J Clin Invest*, 76 (4):1436–9 (1985), prior to sequence analysis. The C-terminal portion of the peptide was isolated by HPLC following cleavage with cyanogen bromide. Matsudaira, P. "Limited N-Terminal Sequence Analysis," *Guide to Protein Purification*. Deutscher ed. Academic Press (1990). Cysteine residues were identified by sulfhydryl reduction followed by reaction with 4-vinylpyridine prior to sequence analyses. Wilde, C. G., J. E. Griffith, et al., "Purification and characterization of human neutrophil peptide 4, a novel member of the defensin family, "*J Biol Chem*, 264 (19): 11200–3 (1989).

EXAMPLE 5

Mass Spectroscopy. Molecular weight of the unreduced peptide was independently determined by fast-atom bombardment on a JEOL HX110 mass spectrometer at 1000 resolution (Structural Biochemistry Center, University of Maryland, Baltimore County) and on a VG analytical ZAB 2-SE high field mass spectrometer operating at Vacc=8 kv (MScan, Inc., West Chester, Pa.).

EXAMPLE 6

PCR Amplification. The PCR product was obtained using the degenerate oligonucleotide 5'-GAGCTCD-GTICCDATYTGYTTCAT, SEQ ID NO:8, as an antisense primer, a 1:1 mixture of 5'-GAATT-CAAYCCHGTBAGiTGYGTT, SEQ ID NO:13, and 5'-GAATTCAAYCCHGTBTCYTGYGTT, SEQ ID NO:7, as sense primers and a pool of bovine tracheal cDNA (prior to size fractionation) as a template. The general protocol for polymerase chain reaction (PCR) amplification; Saiki, R. K., D. H. Gelfand et al., "Primer-directed enzymatic amplification of DNA with a Thermostable DNA polymerase," *Science*, 239:487–91 (1988) using reagents from a Gene Amp kit (Cetus) was modified for using the degenerate primers. Final concentration of template cDNA was 0.2 ng/ml and final concentration of primers was 1μM. After initial denaturation at 94° C. reactions were incubated for 30 cycles of one minute at 94° C., one minute at 55° C. and three minutes at 72° C. Bands were purified by electroelution after electrophoresis in polyacrylamide gels.

EXAMPLE 7 cDNA cloning. The techniques used for cDNA library construction have been described and reagents were from Invitrogen, San Diego, Calif. A unless noted otherwise. Total mRNA was isolated from bovine tracheal epithelium tissue according to the protocol of Chirgwin et al., "Isolation of biologically active ribonucleic acid from sources enriched in ribonuclease," *Biochem.*, 18:5294–99 (1979). Poly (A+) mRNA was selected using oligo dT cellulose columns (3'->5',Inc.). Poly A enriched RNA from bovine tracheal epithelium was reverse transcribed using a commercially available (Invitrogen) oligo dT primer. Second-strand cDNA was synthesized using RNase H digestion of the RNA-DNA hybrids and *E. coli* DNA polymerase I. T4 DNA polymerase was used to polish the blunt-ended cDNA, and then hemiphosphorylated, Not-1/EcoR-1 adaptors were added by blunt-end ligation. A portion (0.3μg) of this cDNA was size-fractionated by agarose gel electrophoresis, and a fraction (300–3000 bp) was recovered by electroelution. The cDNA was ligated to EcoR-1 digested lambda gt10 (Stratagene) and the recombinant phage was packaged using Gigapak-Gold packaging extract (Stratagene). Approximately $5 \times 10^6$ independent phage were obtained and $10^6$ phage were plated at a density of $3 \times 10^4$/150mm plate on a lawn of C600 hfl− *E. coli*. Duplicate lifts were made using Colony-/Plaque Screen filters (DuPont). The filters were screened sequentially using three probes: 5'-AATCCTGT AAGCTGTGTTAGGAATAAAGG-CATCTGTGTGCCGAT-3', SEQ ID NO:11, 5'-AATAAAGGCATCTGTGTGCCGAT-CAGGTGTCCTGGAAGCAT-GAAACAGATTGG-3', SEQ ID NO:12 and the PCR product, PCR-BT40.1 (sequence not determined, the product was derived as detailed in Example 6). The standard conditions for screening were modified: 50° C., 6×SSC for hybridization and wash with the oligonucleotide probes; and 37° C., 5×SSC/20% formamide and 55° C., 6×SSC for hybridization and wash, respectively for the double stranded probe.

Selected clones were plaque purified, and DNA was obtained from liquid lysates. The cDNA inserts were obtained by digestion with EcoRI, and subcloned into Bluescript plasmid (Stratagene).

EXAMPLE 8

Northern blot analysis. Total RNA was fractionated by agarose gel electrophoresis in the presence of formaldehyde and blotted to nylon membranes (Nytran, Schleicher and Schuell) by capillary technique. Sambrook, et al., *Molecular Cloning*, a laboratory manual, 2nd ed., (Cold Spring Harbor Press, Cold Spring Harbor, N.Y.) Radioactive labelled DNA probes were hybridized to the immobilized RNA in 20% Formamide/5×SSC/5×Denhardt's/0.1% SDS at 42° C., and washed in 0.1×SSC/0.1% SDS at 65° C.

EXAMPLE 9

Sothern blot analysis. Genomic DNAs were obtained commercially from Clonetech (Palo Alto, Calif.), or were isolated from bovine blood by standard methods such as modification of methods described by Aldridge, J., et al., *Am. J. Hum. Genet.*, 36:546–564 (1984). DNA was digested with restriction enzymes and size-fractionated by electrophoresis in 1% agarose gels. Transfer of DNA to nylon membranes (Zetabind, Cuno, Inc., Meriden, Conn.) and incubation with probe were according to standard techniques. Sambrook, et al., *Molecular Cloning: a laboratory manual*, 2nd ed., (Cold Spring Harbor Laboratory Press, Cold Spring Harbor, N.Y.).

EXAMPLE 10

In situ hybridization. Tissue was fixed for 4 hours in 4% paraformaldehyde/phosphate buffered saline, followed by dehydration and paraffin embedding. Sections (10μm) were mounted on slides, pretreated and hybridized with indicated sense or antisense oligonucleotides, 3'-end labeled with [$^{35}$S]dATP as described. Jones and Bevins, *J. Biol. Chem.*, 267:23216–23225 (1992) and Young, et al., *Neurosci. Lett.*, 70: 198–203 (1986). Indicated slides were pretreated with RNAse at 10μg/ml for 15 minutes at room temperature before hybridization with antisense probe. Slides were analyzed by dark field photomicroscopy and then stained with hematoxylin and eosin for bright field analysis. Exposure to photographic emulsion was seven days.

EXAMPLE 11

Primer extension. Total mRNA from bovine trachea was annealed with SEQ ID NO: 16 (5' end labelled with [$^{32}$P]ATP and T4 polynucleotide kinase), and extended with Moloney murine leukemia virus reverse transcriptase as described by Sambrook, et al., *Molecular cloning: a laboratory manual*, 2nd ed., Cold Spring Harbor Press, Cold Spring Harbor, N.Y. Extension products were analyzed by electrophoresis on 7% polyacrylamide gels in the presence of 7M urea using a DNA dideoxy-termination DNA sequence ladder as a size standard.

EXAMPLE 12

Antimicrobial assays. Antimicrobial activity during purification was determined by plate assay described in Zasloff, "Magainins a class of antimicrobial peptides, from Xenopus skin: Isolation, characterization of two active forms, and partial cDNA sequence of a precursor," *Proc Natl Acad Sci*, USA, 84:5449–53 (1987). A concentrated aliquot of each fraction (2–5 μl) was spotted onto a lawn of *E. coli* strain D31 (Steiner, H. D., Hultmark, A. et al., "Sequence and specificity of two antibacterial proteins involved in insect immunity," *Nature*, 292:246–248 (1981)) on a petri dish containing 10 g/l Bacto Tryptone, 5g/1 Yeast extract, 0.75% agarose (Sigma), 25mM Tris, pH7.4, 50 mM NaF, and incubated overnight at 37° C.

Minimal inhibitory concentration (MIC) of the peptide was determined by incubating 2.5×10⁴ bacteria in 0.25×Tripticase Soy Broth (TSB) with increasing concentrations of the peptide in 96 well microtiter plates (Corning), overnight at 37° C.

EXAMPLE 13

| Reference | Sequence | SEQ ID NO: |
|---|---|---|
| TAPG9s | 5'-ATAAAGCGGCAATCGCAGTG-3' | 14 |
| TAPG10a | 5'-ACAACCTCAGTGACCAGTGG-3' | 15 |

| Reference | Sequence | SEQ ID NO: |
|---|---|---|
| TAP48A | 5'-CCAAGCAGACAGGACCAGGAAGAGGAGCGCGAGGAGCAGGTGATGGAGCCTCAT-3' | 16 |
| TAP54S | 5'-ATGAGGCTCCATCACCTGCTCCTCGCGCTCCTCTTCCTGGTCCTGTCTGCTTGG-3' | 17 |
| TAP160A | 5'-CCTGATCGGCACACAGATGCCTTTATTCCAAACACAGCTTACAGGATT-3' | 18 |
| TAP113S | 5'AATCCTGTAAGCTGTGTTAGGAATAAAGGCATCTGTGTGCCGATCAGG-3' | 19 |
| TAP118S | 5'CACCTGTGTTGGGCGGGCAGTAAA3' | 20 |

RESULTS

EXAMPLE 14

Figure 1A:
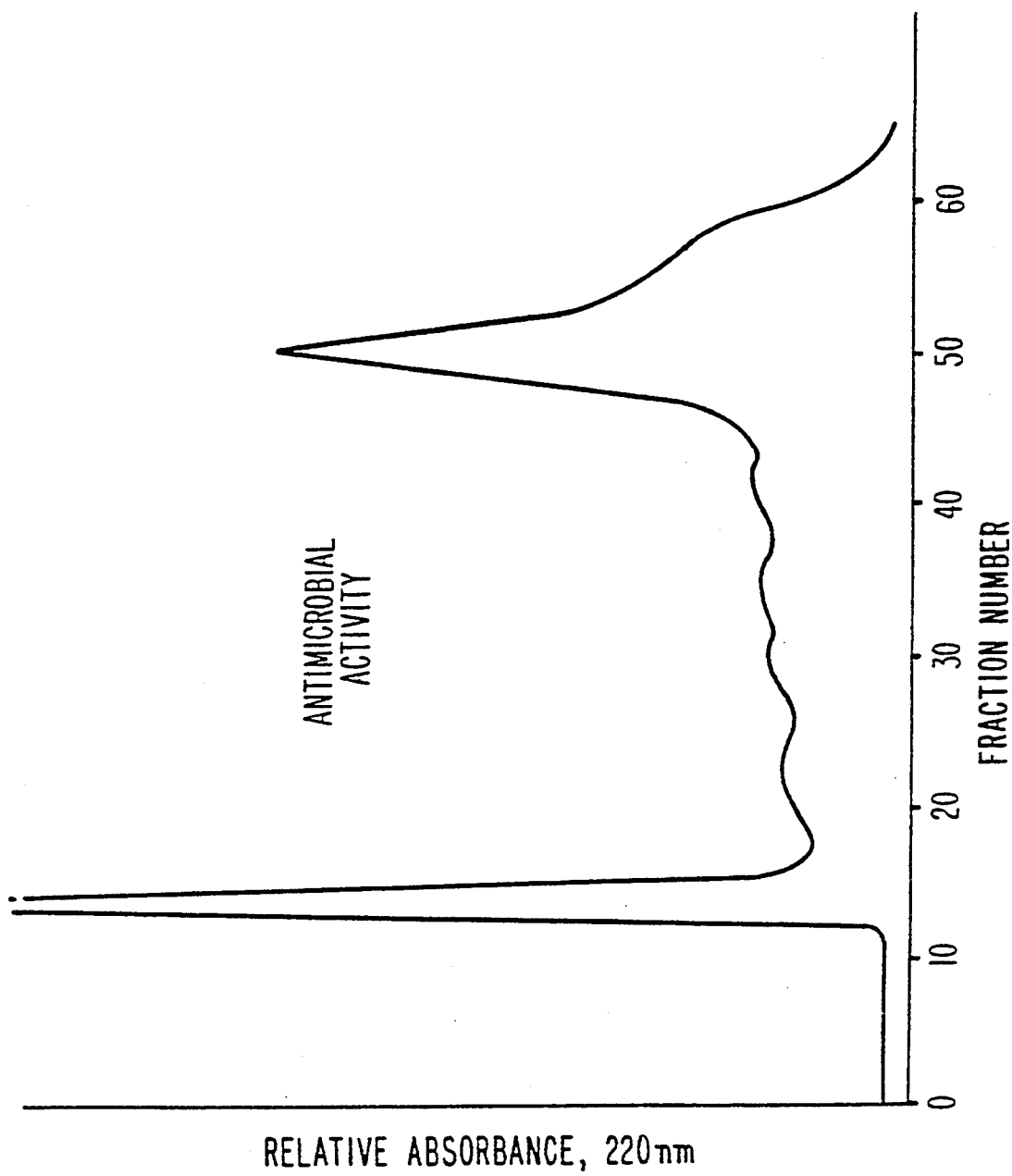
FIG. 1A. P-30 gel filtration chromatogram; fractions containing antimicrobial activity are marked.
Figure 1B:
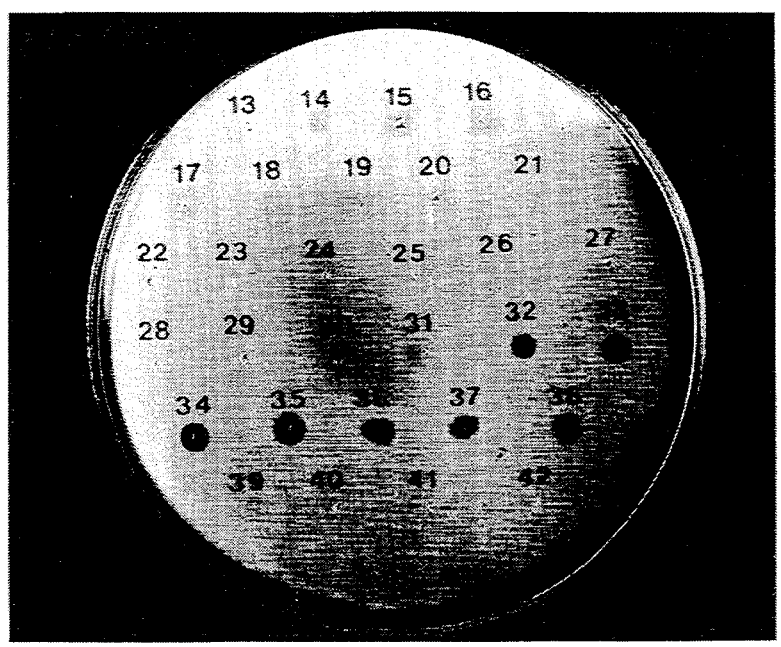
FIG. 1B. Antimicrobial plate assay of P-30 fractions. 2 μl of each fraction was spotted on a lawn of *E. coli* strain D31 and incubated overnight at 37° C.

Isolation of the peptide. The bovine tracheal epithelium was extracted in acid and size-fractionated by gel filtration on Biogel P-30 (FIG. 1A). The elution profile of the tracheal extract showed two peaks of U.V. absorbance (monitored at 220nm). Antibacterial activity was assayed using *E. coli* strain D31 (Steiner, H. D. Hultmark, A., et al., supra (1981)) for fractions 13 (void volume) to 60 (included volume); fractions 32–36 showed significant activity, as evidenced by clear zones of killing (FIG. 1B). These fractions corresponded to the peptide region (i.e., <5,000 Da) when analyzed by SDS-polyacrylamide gel electrophoresis and silver stained for protein (data not shown).

Figure 1C:
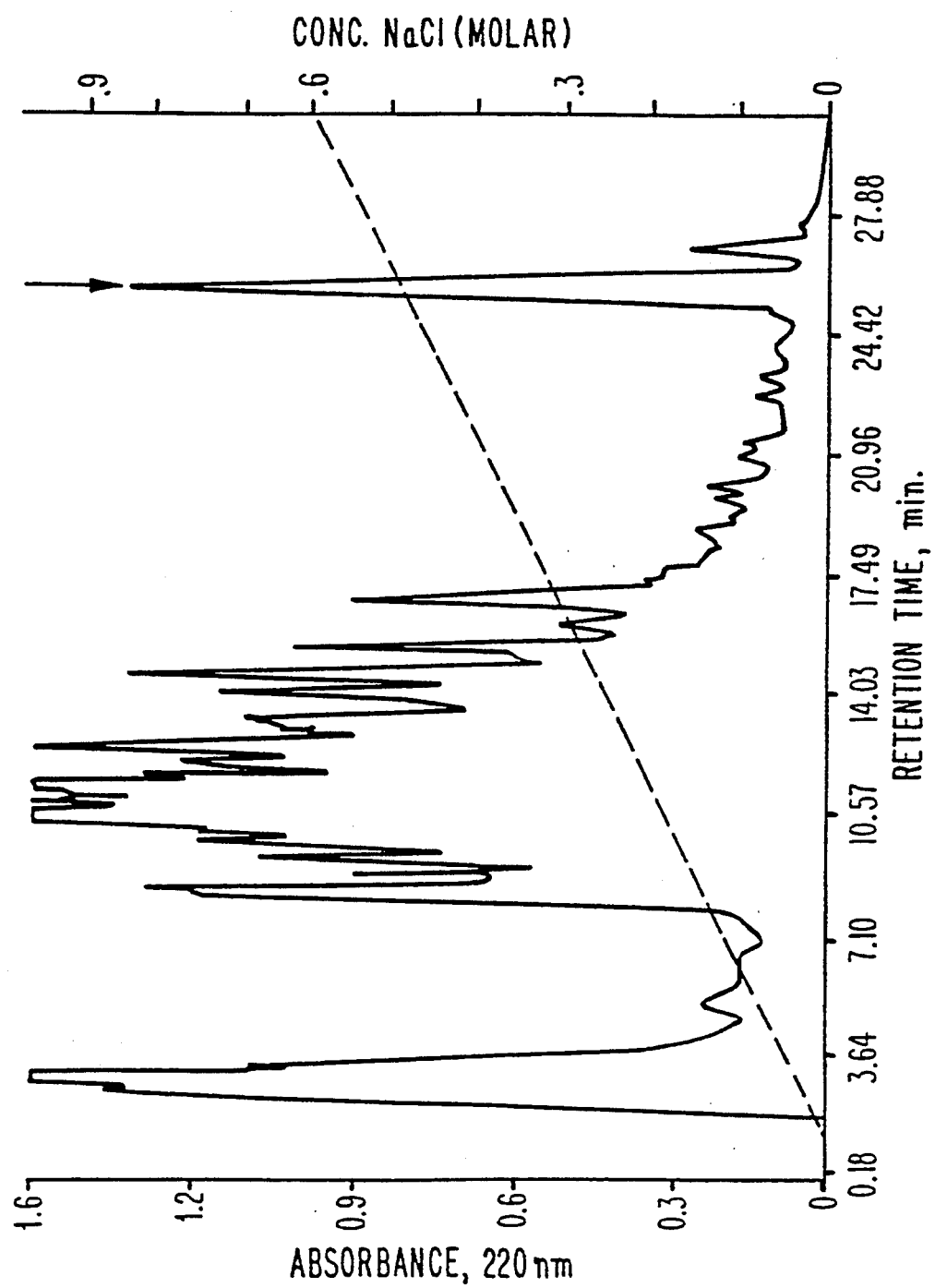
FIG. 1C. Ion exchange HPLC chromatogram of P-30 antimicrobial fractions. Antimicrobial fraction eluting at 26 minutes is marked with an arrow.
Figure 1D:
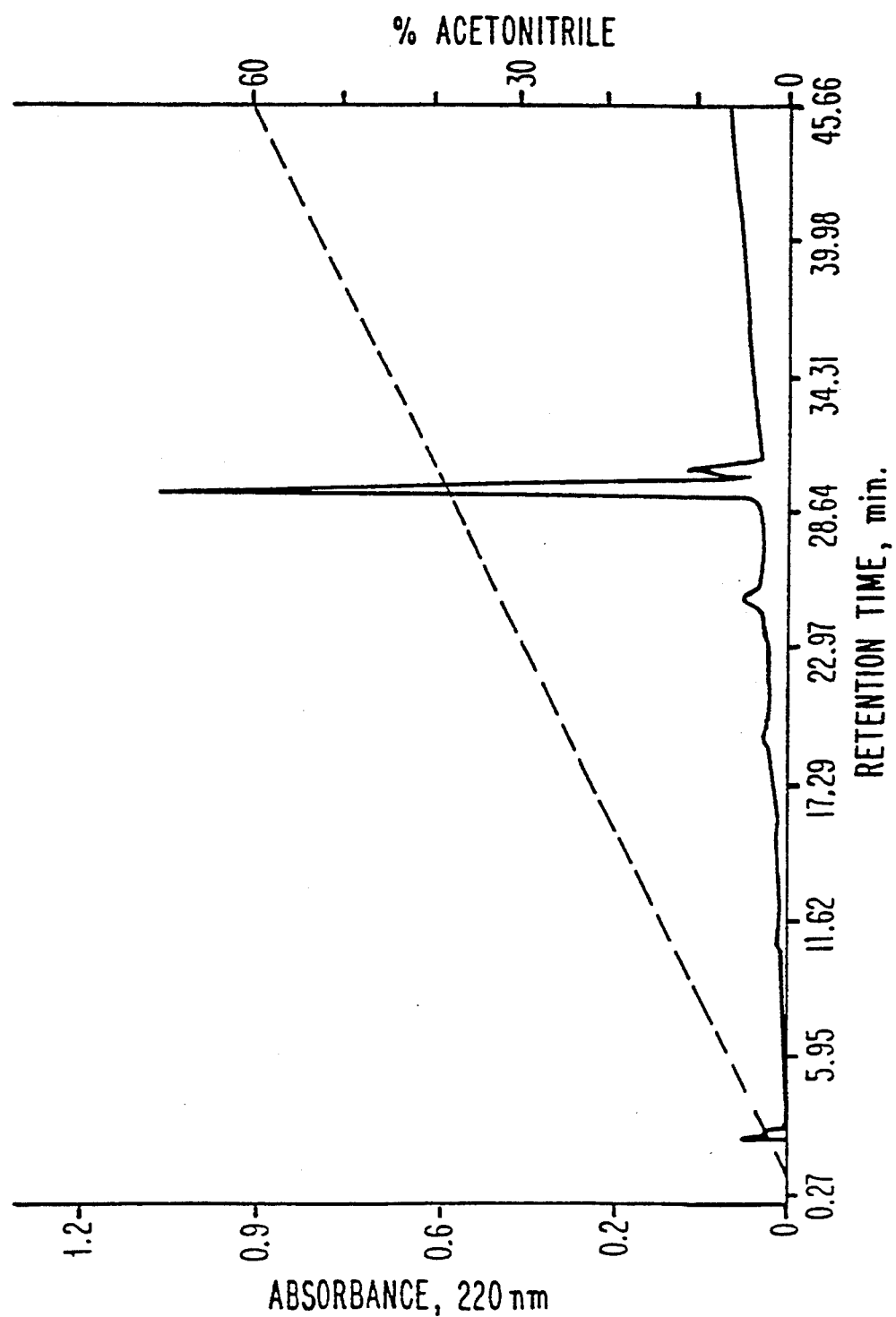
FIG. 1D. Reverse phase HPLC chromatogram of the antimicrobial fraction from ion exchange HPLC.

The antimicrobial fractions were pooled and then fractionated on ion exchange HPLC (FIG. 1C). An isolated peak at 25.6 minutes contained the only detectable antimicrobial activity. This peak was collected and further purified by reverse phase HPLC (FIG. 1D). There was a single superimposed peak of protein (arrow) and antimicrobial activity (data not shown) eluting at 37.3% CH$_3$CN. The overall yield was approximately 2μg/g of epithelium (wet weight). The purity of the peptide was >95% as assayed by analytical HPLC and acid-polyacrylamide gel electrophoresis (data not shown) which showed a single, basic band.

EXAMPLE 15

Protein sequence analysis of TAP. The purified peptide was subjected to protein sequence analysis using automated liquid phase sequencing and amino acid compositional analysis (Table I). The amino-terminal residues were analyzed directly, and the more carboxy-terminal residues were analyzed following cyanogen bromide cleavage (FIG. 2A). The sequence determined by protein sequence analysis predicted a molecular weight of 3443. The molecular weight of the purified peptide was determined by mass spectroscopy analysis to be 4085.5, indicating that the protein sequence was incomplete. It was decided to deduce the remainder of the peptide sequence by analysis of a cloned cDNA.

TABLE I

Amino acid analysis of TAP
Amino acid composition was determined after hydrolysis of 200 pmol of purified TAP (SEQ ID NO: 1). Results are expressed as mol amino acid per mol protein.

| Amino Acid | Analysis (sequence) |
|---|---|
| Asp* | 2.17 (2) |
| Asn | |
| Glu* | 0.83 (1) |
| Gln | |
| Ser | 1.31 (2) |
| Gly | 3.51 (4) |
| Arg | 3.09 (4) |
| Thr | 0.94 (1) |
| Ala | 0.97 (1) |
| Pro | 2.93 (3) |
| Val | 4.59 (5) |
| Met | 1.25 (1) |
| Cys | 3.77 (6) |
| Ile | 2.54 (3) |
| Lys | 3.82 (5) |

*Includes the corresponding amide.

EXAMPLE 16

Cloning of the TAP cDNA. Degenerate-oligonucleotide primers (SEQ ID NO:7, SEQ ID NO:13 and SEQ ID NO:8) were designed corresponding to amino acids 1-6(BT-40-1 and -2) and 21-26 (BT40-3) respectively as shown in FIG. 2B. Sense Primers 1 (SEQ ID NO:7) and 2 (SEQ ID NO:13) had the EcoR1 recognition site incorporated on the 5' end, and antisense primer 3 (SEQ ID NO:8) had the Sst1 recognition site on its 5' end. These primers were used in a PCR using bovine tracheal cDNA as template DNA and were expected to amplify the nucleotide sequence coding for amino acids 1-26. The principal DNA product was 90 bp in length, as expected based on peptide primary structure and the selected oligonucleotide primers. This indicated that cDNA encoding the peptide was present in the library, and yielded a DNA template for probe synthesis.

The cDNA library from bovine tracheal epithelium (approximately 106 independent lambda gt10 phage) was screened using three different probes in parallel: the PCR product (no sequence, product obtained as described in Example 6), and two "best-guess" synthetic oligonucleotide probes (SEQ ID NO:11 and SEQ ID NO:12), designed based on the peptide SEQ ID NO:1 (FIG. 2A) using published codon frequency tables. Lathe, R. "Synthetic oligonucleotide probes deduced from amino acid sequence data. Theoretical and practical considerations," J Mol Biol 183: 1-12, (1985). Only clones which hybridized with two of the three probes (of which there were 15) were considered positive, and 7 of these were taken for further analysis. Several positive clones were plaque purified and the inserts were subcloned into Bluescript plasmid (Stratagene). All inserts were of approximately the same size, and DNA sequence analysis was performed on one of them. The sequence for the cDNA clone pBT40-4.4, SEQ ID NO:4, is shown in FIG. 3.

The cDNA sequence of the precursor protein (FIG. 3, SEQ ID NO:4) contains an open reading frame of 64 amino acids in length from the first ATG codon (base 35). The deduced amino acid sequence of SEQ ID NO:i encoded by nucleotides 113-225 of SEQ ID NO:2, beginning with an N-terminal asparagine residue is in perfect agreement with the amino acid data (FIG. 2D). The open reading frame, which extends 5 residues beyond the most carboxy-terminal residue of the sequence elucidated by peptide analysis, is followed by an in-frame termination codon. The amino acid sequence of the peptide from this clone has a predicted molecular weight of 4091; if all cysteine residues are involved in disulfide bonds, this would reduce the predicted molecular weight to 4085, in complete agreement with the mass spectroscopic data. The amino acid composition of the predicted peptide agrees favorably with the peptide data.

EXAMPLE 17

Figure 4:
FIG. 4. Northern blot analysis of TAP (SEQ ID NO:1) message. Lane 1, 10 μg total bovine trachea RNA; lane 2, 10 μg total bovine lung RNA.

Northern blot analysis. RNA isolated from whole lung and isolated tracheal mucosa was subjected to northern blot analysis using the cDNA insert (SEQ ID NO:4) as a probe (FIG. 4). Under stringent conditions the cDNA (SEQ ID NO:4) probe recognized an abundant message of approximately 400 bp in bovine trachea mRNA, along with a less abundant species of the same size in bovine lung RNA. Both lanes had identical amounts of RNA as evidenced by ethidium bromide staining of the gel (data not shown) and by hybridization to a bovine alpha-tubulin probe (FIG. 4).

EXAMPLE 18

Antimicrobial activity of TAP. The purified bovine TAP, obtained as described herein, was tested on several strains of bacteria to determine its antimicrobial activity in vitro. The results shown in Table II indicate that TAP (SEQ ID NO:1) has antimicrobial activity for both gram positive and gram negative bacteria. In addition, the peptide has significant activity against the fungus Candida albicans. The observed activity of the peptide, SEQ ID NO:1, is on the same order of magnitude as synthetic Magainin-2-NH$_2$ (SEQ ID NO:6), in the assay used here.

TABLE II

Antimicrobial activity of TAP
Antimicrobial activity of TAP (SEQ ID NO: 1) and Magainin 2-NH$_2$ (SEQ ID NO: 6). Minimal inhibitory concentrations were determined by incubating approximately 2.5 × 10$^4$ microbe in 0.25× TSB with 50, 25, 12.5, 6.25 or 3.125 μg/ml of the appropriate peptide.

| | Minimal inhibitory concentration (μg/ml) | |
|---|---|---|
| Organism (ATCC) | Magainin 2-NH$_2$ SEQ ID NO: 6 | TAP SEQ ID NO: 1 |
| Escherichia coli (*) | 3.125–6.25 | 12.5–25 |
| Klebsiella pneumonia (13883) | 3.125–6.25 | 12.5–25 |
| Staphylococcus aureus (25923) | 25–50 | 25–50 |
| Pseudomonas aeruginosa (27853) | 6.25–12.5 | 25–50 |
| Candida albicans (14053) | 25–50 | 6.25–12.5 |

*strain D31 (Steiner, H. D., Hultmark, A., supra, (1981)

EXAMPLE 19

Tissue specific expression of TAP

While TAP was originally isolated from the tracheal mucosa (Diamond, G., et al., (1991) Proc. Natl. Acad. Sci. (USA) 88, 3952-3956), In order to determine if TAP was also expressed in other epithelial tissues, total RNA (10 μg) was isolated from several tissues and studied by northern blot analysis as described in Example 8 using $^{32}$P-end labeled oligonucleotide SEQ ID NO: 18 or α-tubulin cDNA probe used as a control. The results in FIG. 5A show that TAP expression is restricted to airway tissue, with the majority of expression in the trachea, although some mRNA is detected in the nasal septum mucosa. No signal was seen in RNA from bovine fallopian tube, which like the airway is ciliated, nor was there any signal in small intestine. No TAP expression was observed prenatally, as there was no signal in tracheal RNA from two different ages of fetal cows. As a control, the blot was also hybridized with a bovine alpha-tubulin probe, which indicated that relatively similar amounts of RNA were in each sample (FIG. 5A). An RNase protection assay was also performed on the above RNAs by standard procedures described, for example, in Ausubel, et al., *Current Protocols in Molecular Biology*, Vol 1, pp. 3.8.1–3.8.4 (MA General Hospital, 1987). The results were similar to those seen in the Northern, with no signal seen in fallopian tube or fetal trachea (data not shown). Northern blot analysis of other tissues, including testes, salivary glands, kidney and brain also failed to elicit any signal when hybridized with the TAP probe (data not shown).

To further analyze the expression of TAP throughout the bovine conducting airway, and to test for the possible variation in expression between individual cows, a separate northern blot containing tracheal RNA obtained from three different cows (from the same cull), and from the proximal tracheal mucosa, distal tracheal mucosa (near the first division), and bronchiolar tissue (at the third division) was probed. The experiment showed that there was some difference (~2–4 fold) between the three animals examined (FIG. 5B). A modest degree of variation of TAP expression was also seen along the mucosal portion of the airway (FIG. 5B). However, this variation may reflect the abundance of ciliated epithelium obtained in the discussion.

EXAMPLE 20

In situ hybridization of TAP

Figure 6C:
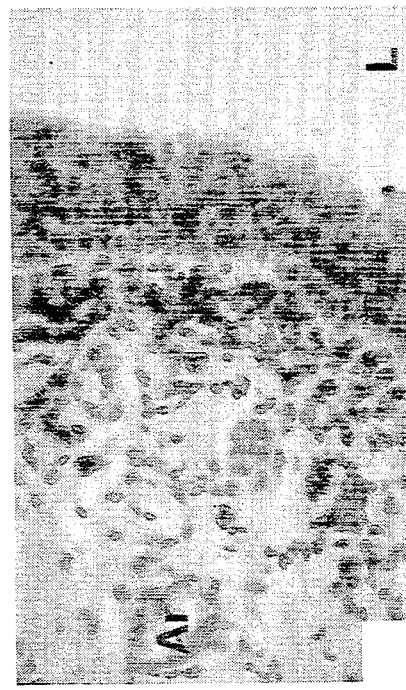
FIG. 6C. Light field photomicrograph of cross section of bovine bronchiolar tissue hybridized with $^{35}$S-labeled with antisense probe TAP160A and stained with hematoxylin and eosin.
Figure 6E:
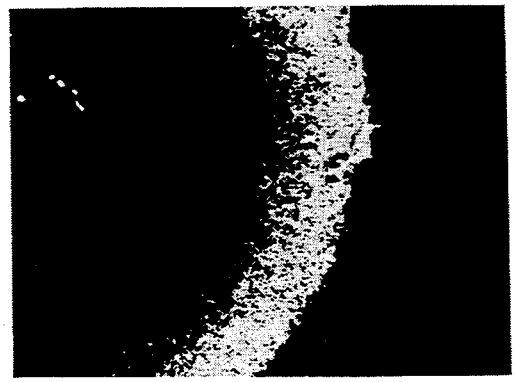
FIG. 6E. Dark field photomicrograph of cross-section of Panel A after pretreatment of tissue with RNase at 10 μg/ml for 15 minutes at room temperature.
Figure 6F:
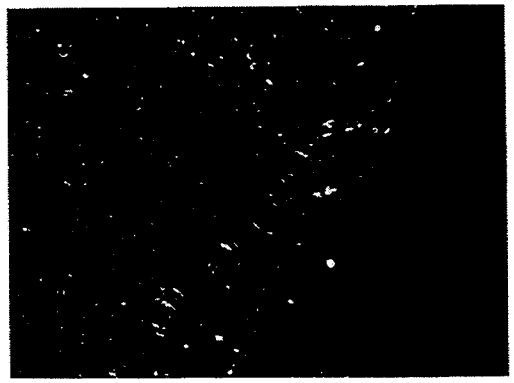
FIG. 6F. Dark field photomicrograph of cross-section of Panel B.
Figure 6G:
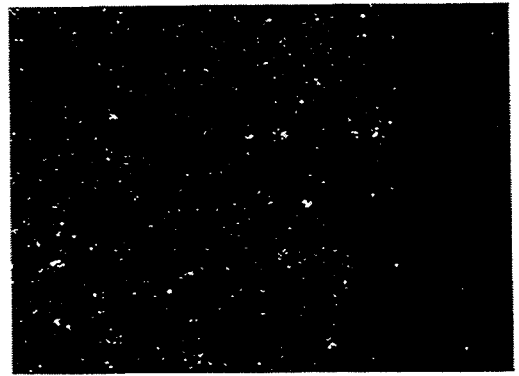
FIG. 6G. Dark field photomicrograph of cross-section of Panel C.
Figure 6H:
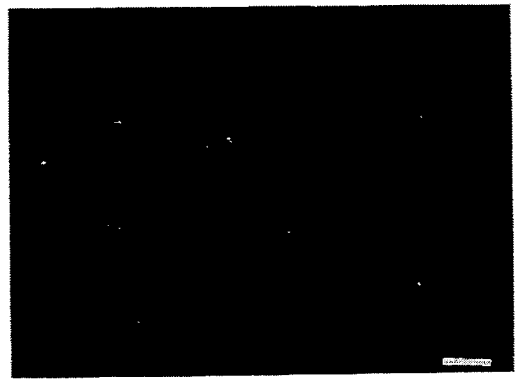
FIG. 6H. Dark field photomicrograph of cross-section of Panel D after pretreatment of tissue with RNase at 10 μg/ml for 15 minutes at room temperature.

In order to further characterize the expression of TAP mRNA in the bovine airway, in situ hybridization was performed on fixed sections of tissue. When hybridized with the $^{35}$S-labelled antisense TAP oligonucleotide probe SEQ ID NO: 18, a highly abundant signal was observed in the epithelial cells lining the airway (FIG. 6A, 6E). Essentially similar results were obtained in cross-sections of proximal and distal tracheal sections (data not shown). No signal was seen in the basal layer of the epithelium (FIG. 6A, 6E), in alveoli (6D, 6H), in connective tissue (6A, 6E) or in glandular cells (data not shown). The complementary sense oligonucleotide probes SEQ ID NO: 19 did not result in any specific signal (FIG. 6B, 6F), consistent with hybridization specific for the TAP message. Also, no signal was observed when the tissue was pretreated with RNase A prior to hybridization with the antisense oligonucleotide (FIG. 6C, 6G).

EXAMPLE 21

Cloning of the TAP gene

A bovine genomic library in EMBL 3 was screened with a TAP oligonucleotide probe SEQ ID NO: 16 and numerous hybridizing plaques of varying intensities were identified. The plaques with strongest signal were purified and then screened with a second TAP oligonucleotide probe SEQ ID NO: 18. One phage (TAPG-3) strongly hybridized with both probes. Preliminary sequence analysis indicated that several of the clones hybridizing to SEQ ID NO: 16 but not SEQ ID NO: 18, encode TAP-like family members (unpublished observations). Southern blot hybridization of the TAPG-3 phage DNA with other probes from the 5′ and 3′ regions of the TAP cDNA sequence indicated that the entire transcribed region of the gene was contained on a single 1.9 kb Eco R1 fragment (data not shown). A restriction map of this fragment along with adjacent sequences is shown in FIG. 7A. The sequence of the entire 1.9 kb Eco R1 fragment plus an additional 1.4 kb of 5′ flanking nucleotides was determined, and is shown in FIG. 8C (SEQ ID NO: 5). Comparison of this sequence with the TAP cDNA indicated that the bovine TAP gene has two exons surrounding a 1.6 kb intron. Primer extension analysis of mRNA from bovine tracheal mucosa exhibits two bands of comparable intensity (FIG. 7B). The size of the shorter product is consistent with transcription initiation from the adenosine which was assigned as nucleotide +1 (see FIG. 8); transcription may thus also initiate from nucleotide −1.

Sequence comparison analysis with GenBank identified several regions upstream of exon 1 with high nucleotide identity to known sequences. The sequence of highest similarity (identify 90% over 542 bases, shown underlined in FIG. 8) is the bovine alu-type art2 sequence, a highly repetitive element found upstream from a number of bovine genes (Duncan, C. H. (1987) *Nuc. Acids Res.* 15, 1340). Other sequences with nucleotide similarity to the TAP 5′ flanking sequence include regions 5′ to the sheep wool keratin microfibril type I gene and the bovine adenylate kinase gene (both with 81% identity), and the goat beta globin gene (67% identity). These comparisons define a flanking segment containing ruminant-specific, repetitive sequences upstream from the TAP transcriptional start site. Consensus sites for eukaryotic transcriptional regulation are also observed upstream from this site. Of particular interest is a TATA box at −24, a CAAT box is at −84, and an NFKB consensus binding sequence at −181.

EXAMPLE 22

Genomic analysis of TAP-related sequences

Many families of antimicrobial peptides maintain high nucleotide identity in the 5′ region of the mRNA (Jones, D. E. and Bevins, C. L. (1992) *J. Biol. Chem.* 267, 23216–23225; Lidholdm, D. -A., et al. (1987) *F.E.B.S. Lett.* 226, 8–12; Ganz, T. et al., (1989) *J. Immunol.* 143, 1358–1365; Ouellette, A. J. and Lualdi, J. C. (1990) *J. Biol. Chem.* 265, 9831–9837; Kylsten, P. et al. (1990) *EMBO* 9, 217–224). To determine if this might be true for TAP, a Southern blot containing bovine genomic DNA was hybridized with an oligonucleotide probe (TAP 48A), corresponding to a 5′ sequence of TAP mRNA. FIG. 9A shows that within the bovine genome there are numerous bands which hybridize to this sequence, under the same stringency as used for our cloning experiments. The multiple bands are consistent with the cloning results described above, the presence of TAP-related sequences in the bovine genomic library was detected. The same blot was subsequently hybridized with two different oligonucleotide probes from the mature peptide-coding region of TAP (SEQ ID NO: 18, FIG. 9B, and SEQ ID NO: 20, FIG. 9C). SEQ ID NO: 18, which encodes the first 16 amino acids of the mature peptide, recognizes fewer bands under the same conditions of stringency: two major bands in the EcoR1 lane, and three in the Taq 1 lane. SEQ ID NO: 20, a shorter oligonucleotide which corresponds to a more C-terminal region of the peptide, yielded single bands in both lanes under comparable stringency. This latter result is consistent with the presence of the TAP gene in a single copy. The multiple bands obtained with the probes SEQ ID NO: 16 and SEQ ID NO: 18 are consistent with the presence of a group of TAP related sequences in the bovine genome. This notion was validated upon sequence analysis of several genomic clones as described above.

One unexpected finding was that the single Eco R1 band in FIG. 9C corresponded to approximately 4.0 kb, while the sequence of the genomic clone indicated that the fragment size containing the probes was 1.9 kb. This discrepancy was reconciled upon the finding that there is a polymorphism at one of the Eco R1 sites flanking the TAP gene, yielding in some cases either a 4.0 kb band or a 1.9 kb band (data not shown). To determine if there were any breed-associated polymorphisms within the transcribed TAP sequence, genomic DNA isolated from blood samples of Holstein, Jersey and Simmenthal cows was subjected to PCR amplification using oligonucleotide primers surrounding the TAP gene. In each case these primers amplified a single segment of DNA which was subcloned and partially sequenced. Sequence analysis indicated that the exon portions of the TAP gene in the three breeds were identical, although there were some single base substitutions within the intron sequence (data not shown).

We claim:

1. A cDNA sequence consisting of the sequence defined in SEQ ID NO: 4.

2. A cDNA sequence consisting of the sequence defined in SEQ ID NO: 2.

3. A purified DNA sequence consisting of the sequence defined in SEQ ID NO: 5.

* * * * *

UNITED STATES PATENT AND TRADEMARK OFFICE
CERTIFICATE OF CORRECTION

PATENT NO. : 5,432,270
DATED : July 11, 1995
INVENTOR(S) : Michael A. Zasloff, Charles L. Bevins & Gill Diamond It is certified that error appears in the above-indentified patent and that said Letters Patent is hereby corrected as shown below:

In column 1, before BACKGROUND OF THE INVENTION, please make reference to the following Government Grant information:

This work was supported in part by National Institute of Health, grant number A132234. The United States government may have certain rights in this invention.

Signed and Sealed this

Twenty-seventh Day of October, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 38 amino acids
        ( B ) TYPE: amino acid
        ( D ) TOPOLOGY: linear ( x i ) SEQUENCE DESCRIPTION: SEQ ID NO:1:

```
Asn Pro Val Ser Cys Val Arg Asn Lys Gly Ile Cys Val Pro Ile
 1               5                  10                   15

Arg Cys Pro Gly Ser Met Lys Gln Ile Gly Thr Cys Val Gly Arg
 20              25                  30

Ala Val Lys Cys Cys Arg Lys Lys
 35
```

( 2 ) INFORMATION FOR SEQ ID NO:2:

( i ) SEQUENCE CHARACTERISTICS:
        ( A ) LENGTH: 114 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:2:

```
AATCCTGTAA GCTGTGTTAG GAATAAAGGC ATCTGTGTGC CGATCAGGTG TCCTGGAAGC    60

ATGAAACAGA TTGGCACCTG TGTTGGGCGG GCAGTAAAAT GCTGTAGAAA GAAG         11
```

( 2 ) INFORMATION FOR SEQ ID NO:3:

( i ) SEQUENCE CHARACTERISTICS:
        ( A ) LENGTH: 64 amino acids
        ( B ) TYPE: amino acid
        ( D ) TOPOLOGY: linear ( x i ) SEQUENCE DESCRIPTION: SEQ ID NO:3:

```
Met Arg Leu His His Leu Leu
 1               5

Leu Ala Leu Leu Phe Leu Val Leu Ser Ala Trp Ser Gly Phe Thr Gln
 10               15                  20

Gly Val Gly Asn Pro Val Ser Cys Val Arg Asn Lys Gly Ile Cys Val
 25              30                  35

Pro Ile Arg Cys Pro Gly Ser Met Lys Gln Ile Gly Thr Cys Val Gly
 40              45                  50                   55

Arg Ala Val Lys Cys Cys Arg Lys Lys
 60
```

( 2 ) INFORMATION FOR SEQ ID NO:4:

( i ) SEQUENCE CHARACTERISTICS:
  ( A ) LENGTH: 349 base pairs
  ( B ) TYPE: nucleic acid
  ( C ) STRANDEDNESS: double
  ( D ) TOPOLOGY: linear ( x i ) SEQUENCE DESCRIPTION: SEQ ID NO:4:

| | | | | | | |
|---|---|---|---|---|---|---|
| CCGCGGCCGC | CGCCGAGCCG | CTCGGGACGC | CAGCATGAGG | CTCCATCACC | TGCTCCTCGC | 60 |
| GCTCCTCTTC | CTGGTCCTGT | CTGCTTGGTC | AGGATTTACT | CAAGGAGTAG | GAAATCCTGT | 12 |
| AAGCTGTGTT | AGGAATAAAG | GCATCTGTGT | GCCGATCAGG | TGTCCTGGAA | GCATGAAACA | 18 |
| GATTGGCACC | TGTGTTGGGC | GGGCAGTAAA | ATGCTGTAGA | AAGAAGTAAA | AGAAGGCCAA | 24 |
| GACACAGCCG | GGATCAATGC | CCAGTCAGAA | ACTGCGCCCT | TTGACAGAGC | GTCTAAAATT | 30 |
| TAAACCAGAA | TAAATTTTGT | TCAAAGTTAA | AAAAAAAAAA | AAAAAAAA | | 34 |

( 2 ) INFORMATION FOR SEQ ID NO:5:

( i ) SEQUENCE CHARACTERISTICS:
    ( A ) LENGTH: 3370 base pairs
    ( B ) TYPE: nucleic acid
    ( C ) STRANDEDNESS: double
    ( D ) TOPOLOGY: linear ( i i ) MOLECULE TYPE: DNA (genomic)

( i x ) FEATURE:
    ( A ) NAME/KEY: CAATsignal
    ( B ) LOCATION: 1382..1389

( i x ) FEATURE:
    ( A ) NAME/KEY: TATAsignal
    ( B ) LOCATION: 1444..1449

( i x ) FEATURE:
    ( A ) NAME/KEY: CDS
    ( B ) LOCATION: 1503..1560

( i x ) FEATURE:
    ( A ) NAME/KEY: CDS
    ( B ) LOCATION: 3074..3211

( i x ) FEATURE:
    ( A ) NAME/KEY: exon
    ( B ) LOCATION: 1502..1560

( i x ) FEATURE:
    ( A ) NAME/KEY: exon
    ( B ) LOCATION: 3074..3211

( i x ) FEATURE:
    ( A ) NAME/KEY: intron
    ( B ) LOCATION: 1..1472

( i x ) FEATURE:
    ( A ) NAME/KEY: intron
    ( B ) LOCATION: 1561..3073

( i x ) FEATURE:
    ( A ) NAME/KEY: intron
    ( B ) LOCATION: 3211..3370

( x i ) SEQUENCE DESCRIPTION: SEQ ID NO:5:

| | | | | | | |
|---|---|---|---|---|---|---|
| AGCCCACCAA | CCCCTCAGTC | CATGGGACTC | ACCAGGCAAG | AACACTGGAG | CGGGTTGCCA | 60 |
| TTTCCTTCTT | CAAAAGGAAC | CATCAGTCCA | GTTCAGTTCA | GTTCAGTTCA | GTCGCTCAGT | 120 |
| GGTACCCAAC | TCTTTGCGAC | CCCATGAATT | GCAGCATGCC | AGGACTCCCT | GTCCATCACC | 180 |
| AACTCCCAGA | GTTCACTCAA | ACTCATGTCC | ATCGAGTCGG | TGATGCCATC | CAACCATCTC | 240 |
| ATCCTCTGTC | GCCCCCTTCT | TCTCCTGCCC | CAAATCCCTC | CCAGCACCAG | GGTCTTTTCC | 300 |
| AATGAGTCAA | CTCTTCGCAT | GAGGTGGCCA | AGGTATTGGA | GCTTCAGCTT | CAGCATGAGT | 360 |

```
CCTTCCAAAG AACACCCAGG ACTGATCTCC TTTAGGATGG ACTGGTTGGA TCTCCTTGCA      420
GTCCAAAAGA CTATCAAGAG TCTTCTCCAA CACCACAGTT CAAAAGCATC AATTCTTTGG      480
CGCTCAGCTT CTTCACAGTC CAACTCTCAC ATCCATACAT GACCACTGGA AAAAACCAT      540
AGGCCTTGAC TAGGCGGACC TTTGTTGGTA AAGTAATATC TCTGCTTTTC AAATGCTATC      600
TAGGTTGGTC ATAACTTTCC TTCCAAGGAG TAATCGTGTT TTAATTTCAT GGCTGCAATC      660
ACCATCTGCC ATGATTTTGG AGCCCCAAAA ATAAAGTCTG ACACTGTTTC CACTGTTTCC      720
CCATCTATTT CCCATGAAGT GATGGGATCA TACGCCATTA TCTTAGTTTT CTGAATGTTG      780
AGCTTTAAGC CAACTTTTTC ACTCTCATCT TTCACTTTCA TCAAGAGGCT TTTTAGTTCC      840
TCTTCACTTT CTGCCATACG GGTGGTGTCA TCTGCATATT TGAGGTTATT GACATTTCTC      900
CCGGCAATCT TGATTCCAGC TTGTGCTTCT TCCAGCCAAT AAGGAACTAT AGAAATAAAG      960
AAAGTGAAGT CACCCAGTCG TGTCTGACTC TGTGCAATCC CATGAACTGT AGCCCACCAG     1020
CCTCCTCCAT CCATGGAATT TTCCAGGCAA GAGTCCTGGA GTGGGGTGCC ATTTCCTTCT     1080
GCACAGGAAA ACAGTGGGCA CTTTCAAAGC CCTGGAAGGG CGAGGGTGGG GCTGGAGAGC     1140
GGGTAAGCGA AGGTTCAGCA AGAAGTCTGT GCCCTGCCAG GGAAACAGGC AAGTCTGTGC     1200
CCCTTGCCAC ACCCCTGCCC ATCAGCTGAA CTGACTGCCG GAAGAAGCTT CTTGTTAAAA     1260
GAGCAGCAGG AAAGCTTTTT CTGGGGTTTT CCCCAGCCTC ATTAGCATAA GAGTGACTGA     1320
CCCTGACCCT GCTTTGTGCC ATAAAGGCCA CTCCCATGAC ACACAGGGAA GAGGATCAGT     1380
TAACCAATTC CTAATAACCA AATCCACAGC CAGCCCAGAA TTCCTCCCGG AACCTGGGAC     1440
CTTTATAAAG CGGCAATCGC AGTGTCTTCT CCAGCATCAG CCGCAGAGCT CGGGACGCCA     1500
GC ATG AGG CTC CAT CAC CTG CTC CTC GCG CTC CTC TTC CTG GTC CTG       1547
   Met Arg Leu His His Leu Leu Leu Ala Leu Leu Phe Leu Val Leu
   1           5                   10                  15
TCT GCT TGG TCA G GTGAGCTCTT GGGAGCCCTG GAGGGAGCCG TGGGCTCTCT        1600
Ser Ala Trp Ser
CTCCTGTTTC TACCTCCTTC TGTCCTGCTA CCCCCATCTA CACGTGGTCA GACTAAACCC     1660
ACCATATTTG ATGCTCCTGA GAAGCCTGCG CTGAGTCCTT AGTAGCGAGA GGGGTCTGAG     1720
AAGGGCCCTG ACAAATTCCT GGCTGTTTCT AATCCACTCT AGTGAGTCCG AGCTTCTGAG     1780
CCCATCTCCT CATTGGTTTC ATGAGGAGGA AACAGAAGAT GTCTCTGTTA AGTGACTCTT     1840
ATTTTTTTCT TTTTCATAAA ACCAAGAAAT TTGATTTTGT CCCATGACAG AAGCACAGAA     1900
TGTCGCTTTA TAAATCTTTA TATCCGAAGG TAGCGGCTCT GGGCAACCAG AGAAGTCCAG     1960
AGGTGAGTCA GGCCAAGCCT GGGCTTTGGG AGCTGCCCTT GGGACACTCC GTGATGAGTC     2020
TCTTCAGCAG GAAAGTCCTC CAGGACACGT CGCTGATGAT GAGACCCTCG CTCCACAGCT     2080
GGGAGGCAGC ACATCCAAAG CAGTGTGCAG GATCGGCTGT CTGATTTTCA TCTTACCCTT     2140
GATATTTCCG GAAATAGGAT GAAAATATGT AGGAAGGAAG GAGGGAGGGA GGGAGAGAGA     2200
GGCTGCAGAG ACTGAGACCT GAGACAACTG ATTAGATGTC AAAATCAAGT TGAAATTCCC     2260
TTGTCTGATC AGTGTTGTTT ATGACTGTAA CCCAACTCTT AGCACAGTGG CAGGGAGAGA     2320
GGACAGGGTG TAAGGAAGAC GGCCTCTCAG TGCCTGGGGC CTGGGTTCAA TCCCTGGAGG     2380
GGGAACTAGA GAAGGACCAG AGGTGCCTTG TGGCCAAAAG AGAAAGGGC CTGTGAGGAA      2440
GGCCCCTGGT CAGGCATGTG AGAGGATGGG AAGGCCGCTG ATCGGGAGGA AACCACAAAG     2500
GGAGGAGGAG AGGGGCTGAC TGGCCCCAGT GCTGAGAGTG TTCCGAGTTA GTACAGATGA     2560
TGATACAAAA CTTTTTTTTC TGAACCATTG TCACTGTCAG CTGGTAAGTT GCTTTGAGAG     2620
TAAGTTCTCT TTAAACAGTT CTTACACTTT CAGCTGCATC TTTTCCTCCT ATCTCAGCTC     2680
TACTACTTGA CTGACTCCAT GAGTCGGAAA ACTAAACAGT GAAAATAGAC CCCTGTGGGC     2740
```

```
CGCTTCTGAC  TCCTGGCGGG  AAGGTGGATG  TAGCAGAGCT  TCCTGGTCTT  TGCCCTTGTG      2800

GTGGAGCTGA  CCCCGCACAC  AAACCGGGGT  CCTCACACCC  CAGTCCCTCA  GCCTCTGGTT      2860

CTGGAAACGT  GAGGGTCCAC  CAGAGCCTGG  GCAGGGTCAC  CGTCTGTCTG  CAAACTGGTC      2920

CACAGGGTCC  TGGACTCACA  TCTTGTTGTC  ACAGAGGCCA  TGTCCGCATC  TCATCACATA      2980

AAGCCCCAGG  GCCTTGCTCA  GAGGGACAC   AGCTGGCCTT  CTCGAGATGC  TGCTTTCCTG      3040

CTGACACGTT  TTTCCCTCTC  TGTTCTCTTT  TTA GGA TTT ACT CAA GGA GTA GGA        3094
                                        Gly Phe Thr Gln Gly Val Gly
                                         1               5
```

```
AAT CCT GTA AGC TGT GTT AGG AAT AAA GGC ATC TGT GTG CCG ATC AGG            3142
Asn Pro Val Ser Cys Val Arg Asn Lys Gly Ile Cys Val Pro Ile Arg
         10                  15                  20

TGT CCT GGA AGC ATG AAA CAG ATT GGC ACC TGT GTT GGG CGG GCA GTA            3190
Cys Pro Gly Ser Met Lys Gln Ile Gly Thr Cys Val Gly Arg Ala Val
         25                  30                  35

AAA TGC TGT AGA AAG AAG TAAAGAAGG CCAAGACACA GCCGGGATCA                    3238
Lys Cys Cys Arg Lys Lys
 40                  45
```

```
ATGCCCAGTC  AGAAACTGCG  CCCTTTGACA  GAGCGTCTAA  AATTTAAACC  AGAATAAATT     3298

TTGTTCAAAG  TTAAAGAATC  TTGCCCACTG  GTCACTGAGG  TTGTTGTGTG  GTGTCTGATC     3358

CCAAATGAAT  TC                                                             3370
```

( 2 ) INFORMATION FOR SEQ ID NO:6:

( i ) SEQUENCE CHARACTERISTICS:
        ( A ) LENGTH: 23 amino acids
        ( B ) TYPE: amino acid
        ( D ) TOPOLOGY: linear ( x i ) SEQUENCE DESCRIPTION: SEQ ID NO:6:

```
Gly Ile Gly Lys Phe Leu His Ser Ala Lys
 1               5                  10

Lys Phe Gly Lys Ala Phe Val Gly Glu Ile
 15                  20

Met Asn Ser
```

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

```
GAATTCAAYC  CHGTBTCYTG  YGTT                                                 24
```

( 2 ) INFORMATION FOR SEQ ID NO:8:

( i ) SEQUENCE CHARACTERISTICS:
        ( A ) LENGTH: 24 base pairs
        ( B ) TYPE: nucleic acids
        ( C ) STRANDEDNESS: single
        ( D ) TOPOLOGY: linear ( x i ) SEQUENCE DESCRIPTION: SEQ ID NO:8:

```
GAGCTCDGTN  CCDATYTGYT  TCAT                                                 24
```

( 2 ) INFORMATION FOR SEQ ID NO:9:

( i ) SEQUENCE CHARACTERISTICS:

(A) LENGTH: 44 base pairs
(B) TYPE: nucleic acid
(C) STRANDEDNESS: single
(D) TOPOLOGY: linear (xi) SEQUENCE DESCRIPTION: SEQ ID NO:9:

AACCCTGTCT CCTGTGTGCG CAACAAGGGC ATCTGTGTGC CCAT    44

(2) INFORMATION FOR SEQ ID NO:10:

(i) SEQUENCE CHARACTERISTICS:
(A) LENGTH: 53 base pairs
(B) TYPE: nucleic acid
(C) STRANDEDNESS: single
(D) TOPOLOGY: linear (xi) SEQUENCE DESCRIPTION: SEQ ID NO:10:

AACAAGGGCA TCTGTGTGCC CATCCGCTGC CCTGGCTCCA TGAAGCAGAT TGG    53

(2) INFORMATION FOR SEQ ID NO:11:

(i) SEQUENCE CHARACTERISTICS:
(A) LENGTH: 44 base pairs
(B) TYPE: nucleic acid
(C) STRANDEDNESS: single
(D) TOPOLOGY: linear (xi) SEQUENCE DESCRIPTION: SEQ ID NO:11:

AATCCTGTAA GCTGTGTTAG GAATAAAGGC ATCTGTGTGC CGAT    44

(2) INFORMATION FOR SEQ ID NO:12:

(i) SEQUENCE CHARACTERISTICS:
(A) LENGTH: 53 base pairs
(B) TYPE: nucleic acid
(C) STRANDEDNESS: single
(D) TOPOLOGY: linear (xi) SEQUENCE DESCRIPTION: SEQ ID NO:12:

AATAAAGGCA TCTGTGTGCC GATCAGGTGT CCTGGAAGCA TGAAACAGAT TGG    53

(2) INFORMATION FOR SEQ ID NO:13:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO:13:

GAATTCAAYC CHGTBAGNTG YGTT    24

(2) INFORMATION FOR SEQ ID NO:14:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:14:

ATAAAGCGGC AATCGCAGTG    20

(2) INFORMATION FOR SEQ ID NO:15:

(i) SEQUENCE CHARACTERISTICS:
(A) LENGTH: 20 base pairs
(B) TYPE: nucleic acid
(C) STRANDEDNESS: single
(D) TOPOLOGY: linear (x i) SEQUENCE DESCRIPTION: SEQ ID NO:15:

ACAACCTCAG TGACCAGTGG                                                                         20

(2) INFORMATION FOR SEQ ID NO:16:

(i) SEQUENCE CHARACTERISTICS:
      (A) LENGTH: 54 base pairs
      (B) TYPE: nucleic acid
      (C) STRANDEDNESS: single
      (D) TOPOLOGY: linear (x i) SEQUENCE DESCRIPTION: SEQ ID NO:16:

CCAAGCAGAC AGGACCAGGA AGAGGAGCGC GAGGAGCAGG TGATGGAGCC TCAT           54

(2) INFORMATION FOR SEQ ID NO:17:

(i) SEQUENCE CHARACTERISTICS:
      (A) LENGTH: 54 base pairs
      (B) TYPE: nucleic acid
      (C) STRANDEDNESS: single
      (D) TOPOLOGY: linear (x i) SEQUENCE DESCRIPTION: SEQ ID NO:17:

ATGAGGCTCC ATCACCTGCT CCTCGCGCTC CTCTTCCTGG TCCTGTCTGC TTGG           54

(2) INFORMATION FOR SEQ ID NO:18:

(i) SEQUENCE CHARACTERISTICS:
      (A) LENGTH: 48 base pairs
      (B) TYPE: nucleic acid
      (C) STRANDEDNESS: single
      (D) TOPOLOGY: linear (x i) SEQUENCE DESCRIPTION: SEQ ID NO:18:

CCTGATCGGC ACACAGATGC CTTTATTCCA AACACAGCTT ACAGGATT                  48

(2) INFORMATION FOR SEQ ID NO:19:

(i) SEQUENCE CHARACTERISTICS:
      (A) LENGTH: 48 base pairs
      (B) TYPE: nucleic acid
      (C) STRANDEDNESS: single
      (D) TOPOLOGY: linear (x i) SEQUENCE DESCRIPTION: SEQ ID NO:19:

AATCCTGTAA GCTGTGTTAG GAATAAAGGC ATCTGTGTGC CGATCAGG                  48

(2) INFORMATION FOR SEQ ID NO:20:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (x i) SEQUENCE DESCRIPTION: SEQ ID NO:20:

CACCTGTGTT GGGCGGGCAG TAAA                                                                    24